United States Patent [19]

Nakajima et al.

[11] Patent Number: 4,990,614

[45] Date of Patent: Feb. 5, 1991

[54] N-HETEROCYCLIC AMIDES

[75] Inventors: Terumi Nakajima; Koichi Shudo, both of Tokyo; Giichi Goto, Osaka, all of Japan

[73] Assignee: Takeda Chemical Industries, Ltd., Osaka, Japan

[21] Appl. No.: 253,679

[22] Filed: Oct. 5, 1988

[30] Foreign Application Priority Data

Oct. 6, 1987 [JP] Japan .................. 62-251862
Jun. 23, 1988 [JP] Japan .................. 63-155475

[51] Int. Cl.$^5$ .................. C07D 211/16; C07D 241/04; C07D 243/08; C07D 257/02; C07D 259/00
[52] U.S. Cl. ........................ 540/474; 544/391; 546/247; 540/492
[58] Field of Search .................. 544/391; 540/474; 546/247

[56] References Cited

PUBLICATIONS

N. Kawai, 8th Conference en Neurobiologie, Nov. 25, 1983, Gif, France, Lecture Summaries, p. 10.
N. Kawai, A. Miwa, T. Abe, Advances in Biological Psycopharmacology, 37, 221–227 (1983).
T. Abe, N. Kawai, A. Miwa, J. Physiol., 339, 243–252 (1983).
N. Kawai, A. Miwa, T. Abe, Biomed. Res. 3 353–355 (1982).
N. Kawai, S. Yamagishi, M. Saito, K. Furuya, Brain Res. 278 346–349 (1983).
Chemical Abstracts, vol. 105, No. 21, Nov. 24, 1986, p. 227, Abstract No. 186106d, Columbus, Ohio, E. V. Grishin, "Structure-Functional Characterization of Argiopine an Ion Channel Blocker from the Venom of the Spider . . . ".
N. Kawai, A., Miwa, T. Abe, Brain Res. 247, 169–171, (1982).
N. Kawai, A. Miwa, M. Saito, M. Yoshioka, Microelectrophoretic Investigations of Mammalian Central Transmitters, Aug. 25, 1983, Camberra, Australia, Lecture Summaries, p. 4.
N. Kawai, A. Miwa, M. Saito, M. Yoshioka, 29th Congress of the International Union of Physiological Sciences, Aug. 29, 1983, Sydney, Australia, Lecture Summaries p. 89.

*Primary Examiner*—David B. Springer
*Attorney, Agent, or Firm*—Antonelli, Terry, Stout & Kraus

[57] ABSTRACT

A compound of the formula:

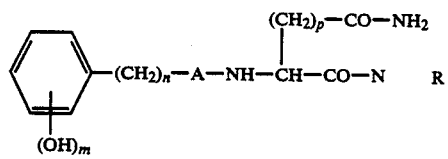

wherein

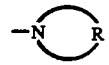

represents a cyclic amino group, A represents a methylene group or a carbonyl group, m represents an integer of 1 to 3, n represents an integer of 0 to 4 and p represents an integer of 1 to 2, or a salt thereof, which has glutamate receptor inhibiting activity is provided.

32 Claims, No Drawings

N-HETEROCYCLIC AMIDES

BACKGROUND OF THE INVENTION

1. Field of the Invention

The present invention relates to a novel amide compound having a glutamate receptor inhibiting activity and salts thereof.

2. Description of the Prior Art

The presence of chemical substances in spiders which paralyze the nerve of anthropodes such as insects has been elucidated and such substances have been isolated. It has also been confirmed that the nerve paralyzing action of those substances is due to glutamic receptor inhibiting action [N. Kawai, A. Miwa, T. Abe, Brain Res., 247 169–171 (1982); N. Kawai, A. Miwa, M. Saito, M. Yoshioka, Microelectrophoretic Investigations of Mammalian Central Transmitters, Aug. 25, 1983, Camberra, Australia, Lecture Summaries p. 4; N. Kawai, A. Miwa, M. Saito, M. Yoshioka, 29th Congress of the International Union of Physiological Sciences, Aug. 29, 1983, Sydney, Australia, Lecture Summaries p. 89; N. Kawai, 8th Conference en Neurobiologie, Nov. 25, 1983, Gif, France, Lecture Summaries, p. 10; N. Kawai, A. Miwa, T. Abe, Advances in Biological Psycopharmacology, 37 221–227 (1983); T. Abe, N. Kawai, A. Miwa, J. Physiol., 339 243–252 (1983); N. Kawai, A. Miwa, T. Abe, Biomed. Res. 3 353–5 (1982); N. Kawai, S. Yamagishi, M. Saito, K. Furuya, Brain Res. 278 346–349 (1983); and Japanese Patent Kokai No. 60-184021 published on June 19, 1985]. Some of chemical structures are reported. For instance, "Proceedings of the Japan Academy", 62 Ser. B, 359 (1986) discloses $N^1$-(2,4-dihydroxyphenylacetylasparaginyl)-$N^5$-(arginylcadaverino-$\beta$-alanyl) cadaverine and the like and Chemical Abstracts, 105: 186106d (1986) discloses (2,4-dihydroxyphenylacetylasparaginyl)-polyamine-(arginyl) wherein the polyamine is —NH(CH$_2$)$_3$NH(CH$_2$)$_3$NH(CH$_2$)$_5$NH—.

Problems come up what is the essence of the action of the glutamate receptor substances including the above chemical substances and what chemical modification is possible.

The inventors synthesized compounds having a part of the structure of the above chemical substances and the above chemical substances which were chemically modified and studied their glutamate receptor inhibiting action to find that the glutamate receptor inhibiting action is developed by bonding a certain group to the partial structure of the above chemical substances. As a result of further investigation, the present invention has been accomplished.

SUMMARY OF THE INVENTION

That is, the compound of the present invention is a compound represented by the formula:

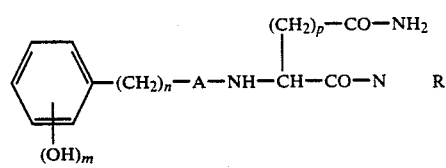

wherein

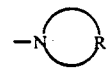

represents a cyclic amino group, A represents a methylene group or a carbonyl group, m represents an integer of 1 to 3, n represents an integer of 0 to 4 and p represents an integer of 1 to 2, or a salt thereof (referred to as "compound [I]" hereinafter).

DESCRIPTION OF THE INVENTION

In the compound [I],

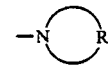

represents a cyclic amino group, namely, a group formed by elimination of hydrogen atom from HN in the cyclic amine represented by

The cyclic amines represented by

are preferably those of 5- to 24-membered ring. The number of nitrogen atoms constituting the ring is normally 1 to 8, preferably 2 to 6. Ring constituting atoms other than nitrogen atom may be oxygen atom and sulfur atom in addition to carbon atoms. Further, the ring may contain a double bond. The amine have preferably molecular weight not more than 500.

As the cyclic amines represented by

mention may be made of, for example, pyrrole, pyrrolidine, imidazole, imidazolidine, pyrazole, oxazolidine, thiazolidine, piperidine, piperazine, morpholine, 1H-azepine, hexahydroazepine, hexahydrodiazepine (e.g., 1,4-), azacyclooctane, diazacyclooctane (e.g., 1,5-), triazacyclononane (e.g., 1,4,7-), tetraazacyclododecane (e.g., 1,4,7,10-), tetraazacyclotetradecane (e.g., 1,4,8,11-), tetraazacyclohexadecane (e.g., 1,5,9,13-), hexaazacyclooctadecane (e.g., 1,4,7,10,13,16-), and octaazacyclotetracosane (e.g., 1,4,7,10,13,16,19,22-). Nitrogen atom and/or carbon atom which constitute R portion of cyclic amine

may have a substituent. Substituent which bonds to nitrogen atom constituting the R portion includes, for example, a lower alkyl group such as methyl, ethyl, propyl or butyl, an aryl group such as phenyl and an aralkyl group such as benzyl or benzhydryl. Substituent which bonds to carbon atom in the R portion has molecular weight of not more than 60 and includes, for example, a lower alkyl group such as methyl, ethyl, propyl or butyl, a lower alkylidene group such as methylene or ethylidene, an oxo group and a thioxo group. These substituents may combine to form a condensed ring. Such condensed cyclic amines include, for example, indole, 1H-indazole, purine, indoline, 1H-benzotriazole, phenoxazin, phenothiazine and carbazole.

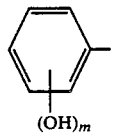

(OH)$_m$ in compound [I] indicates that 1 to 3 hydroxyl to any of 2, 3, 4, 5 and 6 positions of the benzene ring and examples thereof are 2-hydroxyphenyl, 3-hydroxyphenyl, 4-hydroxyphenyl, 2,4-dihydroxyphenyl, 3,4-dihydroxyphenyl and 2,4,5-trihydroxyphenyl.

Compound [I] may be a salt with an inorganic acid or organic acid. Examples of salt of inorganic acid are hydrochlorides, sulfates, carbonates and nitrates and examples of salt of organic acid are formates, acetates, propionates, oxalates, succinates, benzoates and paratoluenesulfonates. Preference is hydrochloride. Further, compound [I] may be a complex salt with a metal such as calcium, zinc, magnesium, cobalt, copper or iron. Amino acid which constitutes compound [I] may be of L-form, D-form or DL-form and L-form is more preferred.

Compound [I] is able to be produced, for example, by the following processes [(1), (2)].

(1) Compound [I] is able to be produced by allowing carboxylic acid [II] of the formula:

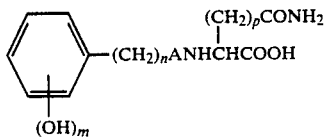

wherein the symbols are the same as defined above, or a salt or a reactive derivative thereof (referred to as compound [II] hereinafter) to react with a cyclic amine

or a salt thereof and, if necessary, eliminating a protecting group (Reaction formula 1).

Reaction formula 1

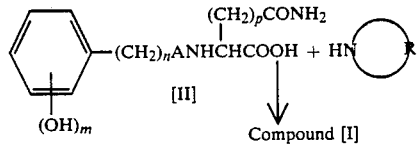

In the above reaction formula 1, the starting compound [II] may be a salt or a reactive derivative thereof and cyclic amine

may be a salt.

The salt of compound [II] includes inorganic base salts or organic base salts of [II]. Examples of the inorganic base salts of [II] are alkali metal salt, e.g., sodium salt and potassium salt and alkaline earth metal salts, e.g., calcium salt. Examples of the organic base salts of [II] are trimethylamine salt, triethylamine salt, tert-butyldimethylamine salt, cyclohexylamine salt, dibenzylmethylamine salt, benzyldimethylamine salt, N,N-dimethylaniline salt, pyridine salt and quinoline salt. The reactive derivative of the starting compound [II] means a reactive derivative at the carboxyl group of the compound. The reactive derivative of compound [II] includes acid halides, acid azides, acid anhydrides, mixed acid anhydrides, active amides, active esters and active thioesters. Examples of acid halides of [II] are acid chloride and acid bromide. Examples of the mixed acid anhydrides are monoalkylcarbonic acid-mixed acid anhydrides, e.g., mixed acid anhydrides of [II] with monomethylcarbonic acid, monoethylcarbonic acid, monoisopropylcarbonic acid, monoisobutylcarbonic acid, mono-tert-butylcarbonic acid, monobenzylcarbonic acid, mono(p-nitrobenzyl)carbonic acid or monoallylcarbonic acid, aliphatic carboxylic acid-mixed acid anhydrides, e.g., mixed acid anhydrides of [II] with acetic acid, trichloroacetic acid, cyanoacetic acid, propionic acid, butyric acid, isobutyric acid, valeric acid, isovaleric acid, pivalic acid, trifluoroacetic acid, trichloroacetic acid or acetoacetic acid, aromatic carboxylic acid-mixed acid anhydrides, e.g., mixed acid anhydrides of [II] with benzoic acid, p-toluic acid or p-chlorobenzoic acid and organic sulfonic acid-mixed acid anhydrides, e.g., mixed acid anhydrides of [II] with methanesulfonic acid, ethanesulfonic acid, benzenesulfonic acid or p-toluenesulfonic acid. Examples of the active amides are amides with nitrogen-containing heterocyclic compounds, e.g., acid amides of [II] with pyrazole, imidazole or benzotriazole and these nitrogen-containing heterocyclic compounds may have a substituent such as an alkyl group, an alkoxy group, halogen atom, an oxo group, a thioxo group or an alkylthio group. As active esters of [II], there may be used all of those which are used for synthesis of peptides. Examples thereof include, in addition to organic phosphates, e.g., diethoxy phosphate and diphenoxy phosphate, p-nitrophenyl ester, 2,4-dinitrophenyl ester, cyanomethyl ester, pentachlorophenyl ester, N-hydroxysuccinimide ester, n-hydroxyphthalimide ester, 1-hydroxybenzotriazole ester, 6-chloro-1-hydroxybenzotriazole ester and 1-hydroxy-1H-2-pyridone ester. Examples of the active thioesters of [II] include esters with aromatic heterocyclic thiol compounds, e.g., 2-pyridylthiol ester and 2-benzothiazolylthiol ester and these heterocyclic rings may have a substituent such as an alkyl group, an alkoxy group, halogen atom or an alkylthio group. One to three hydroxyl groups on the benzene ring of the starting compound [II] may be protected. As examples of the protecting groups, mention may be made of substituted or unsubstituted alkanoyl groups, e.g., acetyl, propionyl and trifluoroacetyl, substituted oxycarbonyl groups, e.g., methoxycarbonyl, ethoxycarbonyl, isopropoxycarbonyl, tert-butoxycarbonyl, phenoxycarbonyl, benzyloxycarbonyl, p-methylbenzyloxycarbonyl or benzhydryloxycarbonyl, a tert-butyl group, aralkyl groups, e.g., benzyl, p-methylbenzyl, p-methoxybenzyl, p-chlorobenzyl, benzhydryl and trityl and substituted silyl groups, e.g., trimethylsilyl and tert-butyldimethylsilyl.

The salt of the cyclic amine

includes salts with inorganic acids of organic acids. Examples of the inorganic acid salts include hydrochloride, hydrobromide, sulfate, nitrate and phosphate. Examples of the organic acid salts include formate, acetate, trifluoroacetate, methanesulfonate and p-toluenesulfonate.

Preparation of salts or reactive derivatives of [II] and of salts of cyclic amine and introduction of a protecting group into [II] is easily performed by known processes or similar processes thereto. For reaction between compound [II] and cyclic amine, for example, a reactive derivative of starting compound [II] as a substance isolated from a reaction mixture may be allowed to react with cyclic amine. Alternatively, a reaction mixture as such which contains the reactive derivative of starting compound [II] which is left unisolated may be allowed to react with cyclic amine. A reaction between the cyclic amine and [II] which is free acid or a salt form is effected in the presence of a suitable condensation agent. The condensation agent includes, for example, N,N'-disubstituted carbodiimides such as N,N'-dicyclohexylcarbodiimide, azolides such as N,N'-carbonyldiimidazole, and N,N'-thiocarbonyldiimidazole, dehydrating agents such as N-ethoxycarbonyl-2-ethoxy-1, 2-dihydroquinoline, phosphorus oxychloride and alkoxyacetylene and 2-halogenopyridinium salts such as 2-chloropyridiniummethyl iodide and 2-fluoropyridiniummethyl iodide. In the case of using these condensation agents, reaction is considered to proceed through the reactive derivative of [II]. The reaction of compound [II] and the cyclic amine is usually carried out in a solvent. Suitable solvent is selected from those which do not harm to the reaction. Examples of the solvent include ethers such as dioxane, tetrahydrofuran, diethyl ether, tert-butylmethyl ether, diisopropyl ether and ethylene glycol-dimethyl ether, esters such as ethyl formate, ethyl acetate and butyl acetate, halogenated hydrocarbons such as dichloromethane, chloroform, carbon tetrachloride, trichlene and 1,2-dichloroethane, hydrocarbons such as hexane, benzene and toluene, amides such as formamide, N,N-dimethylformamide and N,N-dimethylacetamide, ketones such as acetone, methyl ethyl ketone and methyl isobutyl ketone, nitriles such as acetonitrile and propionitrile and besides dimethylsulfoxide, sulforun, hexamethylphosphoroamide and water. These may be used alone or as mixed solvents. Amount of the cyclic amine used is usually 1-5 mol, preferably 1-3 mol per mol of starting compound [II].

The reaction is effected at a temperature of $-80°$–$80°$ C., preferably $-40°$–$50°$ C., most preferably $-30°$–$30°$ C. Reaction time varies depending on varieties of starting compounds [II] and cyclic amine, variety of solvent including mixing ratio in the case of mixed solvent and reaction temperature and is usually 1 minute–72 hours, preferably 15 minutes–3 hours.

In case an acid halide of [II] is used as compound [II], the reaction may be effected in the presence of a deoxidizer for removal of hydrogen halide generated from the reaction system. As the deoxidizer, mention may be made of, for example, inorganic bases such as sodium carbonate, potassium carbonate, calcium carbonate and sodium bicarbonate, tertiary amines such as triethylamine, tripropylamine, tributylamine, diisopropylethylamine, cyclohexyldimethylamine, pyridine, lutidine, γ-collidine N,N-dimethylaniline, N-methylpiperidine, N-methylpyrrolidine and N-methylmorpholine and alkylene oxides such as propylene oxide and epichlorohydrin.

The objective compound [I] of the present invention is obtained by allowing compound [II] to react with cyclic amine as mentioned above and, if necessary, elimination of the protecting group and purification. Elimination of the protecting group for hydroxyl group is effected by the process as it is which is usually employed in the field of synthesis of peptides. For example, methoxycarbonyl, ethoxycarbonyl, tert-butoxycarbonyl or phenoxycarbonyl is eliminated by acids, for example, hydrochloric acid or trifluoroacetic acid, benzyloxycarbonyl, p-methylbenzyloxycarbonyl or benzhydryloxycarbonyl is eliminated by catalytic reduction, benzyl, p-methylbenzyl, p-methoxybenzyl, p-chlorobenzyl, benzhydryl or trityl is eliminated by acids, for example, trifluoroacetic acid or catalytic reduction and trimethylsilyl or tert-butyldimethylsilyl is eliminated by water alone or in the presence of acetic acid.

When elimination of a protecting group is carried out, hydroxyl group-protected compound [I] which has been isolated from a reaction mixture obtained from the reaction of compound [II] and cyclic amine may be subjected to elimination of a protecting group. Alternatively, the reaction mixture may be subjected as it is to elimination of a protecting group. Purification of the hydroxyl group-protected compound [I] or the objective compound [I] is carried out by the known methods such as extraction, gel filtration, ion-exchange resin column chromatography, silica gel thin-layer chromatography, high-performance liquid chromatography and recrystallization.

Process for production of compound [II] will be explained below. Reference is made to, for instance, preparation of compound [I] of the present invention where m is 2, the substituent hydroxyl groups are located at 2- and 4-positions, n is 1 and A is a carbonyl group. Preparation of 2,4-dibenzyloxyphenylacetyl-L-asparagine or glutamine p-nitrophenyl ester [IIa] is explained, since it is especially useful as a starting material [II]. For instance, [IIa] is produced from 2,4-dihydroxybenzaldehyde [IV], through the route shown in the reaction formula 2.

Reaction Formula 2

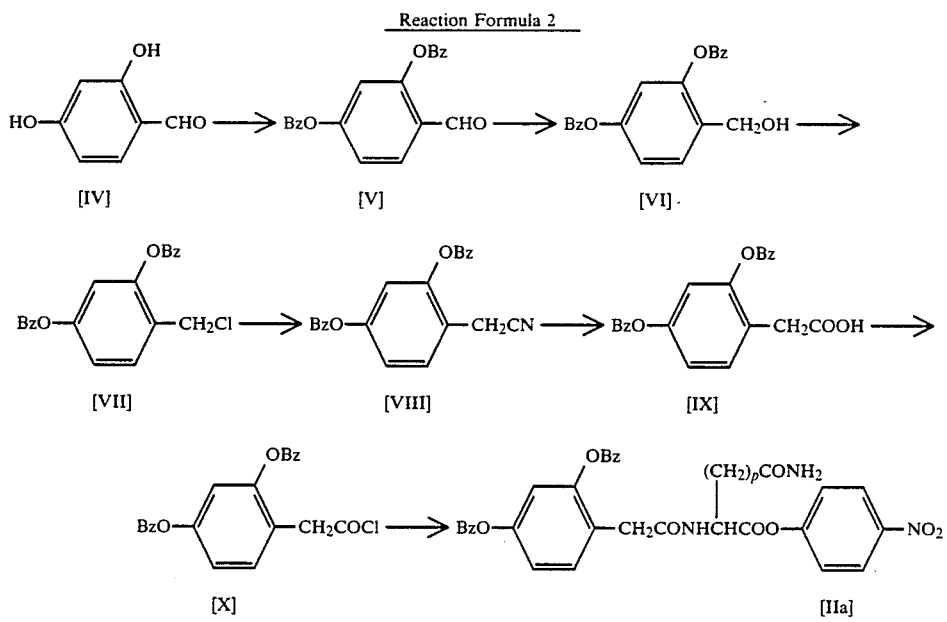

[in the above formula, Bz denotes a benzyl group].

That is, 2,4-dihydroxybenzaldehyde [IV] is benzylated with benzyl chloride to produce 2,4-dibenzyloxybenzaldehyde [V], then [V] is reduced with sodium borohydride to produce 2,4-dibenzyloxybenzyl alcohol [VI] and then, [VI] is chlorinated with thionyl chloride to produce 2,4-dibenzyloxybenzyl chloride [VII]. Then, [VII] is allowed to react with sodium cyanide to obtain 2,4-dibenzyloxyphenyl acetonitrile [VIII], thereafter [VIII] is hydrolyzed with an alkali to produce 2,4-dibenzyloxyphenylacetic acid [IX], then this [IX] is chlorinated with thionyl chloride to produce 2,4-dibenzyloxyphenylacetyl chloride [X] and further, this [X] is allowed to react with L-asparagine or glutamine p-nitrophenyl ester to obtain [IIa].

A preferred compound [II] where the symbol A in the formula is a methylene group is N$^\alpha$-(2,4-dibenzyloxyphenetyl)-L-aspargine (or glutamine) p-nitrophenyl ether [IIb]. The compound [IIb] is prepared, for example, from 2,4-dibenzyloxyphenyl acetaldehyde [XI] via the reaction formula 2-2 hereinbelow mentioned.

Reaction Formula 2-2

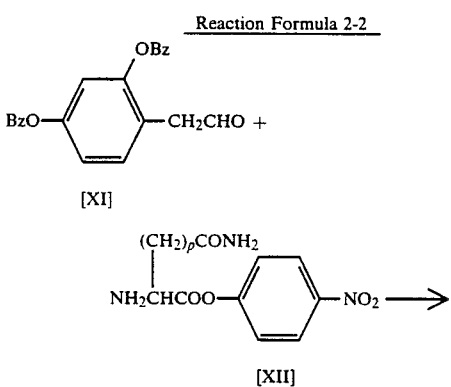

-continued
Reaction Formula 2-2

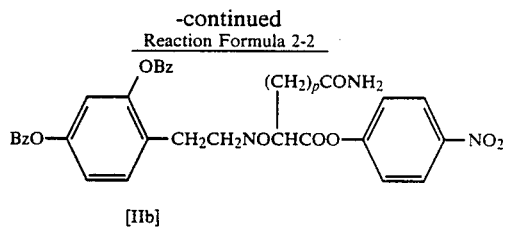

In other words, 2,4-dibenzyloxyphenyl acetaldehyde [XI] is allowed to react with L-asparagine (or glutamine) p-nitrophenyl ester [XII] in the presence of a reducing agent such as sodium borohydride and sodium cyanoborohydride.

(2) When symbol A in the formula is a carbonyl group:

Compound [I] is produced by allowing carboxylic acid [III] of the formula:

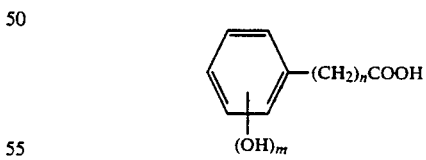

wherein the symbols are as defined above, or a salt or a reactive derivative thereof (referred to as "compound III" hereinafter) to react with compound [IV] of the following formula [IV] or a salt thereof (referred to as "compound IV" hereinafter) and, if necessary, eliminating a protecting group (Reaction formula 3).

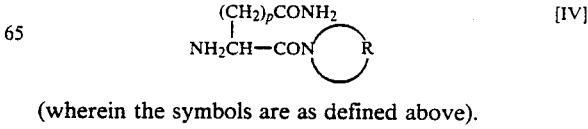

(wherein the symbols are as defined above).

Reaction Formula 3

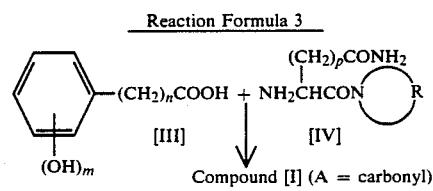

In the above formula 3, the starting compound [III] may be a salt or a reactive derivative. The salt of compound [III] includes inorganic base salts and organic base salts as mentioned for salts of compound [II]. The reactive derivatives of compound [III] includes acid halides, acid azides, acid anhydrides, mixed acid anhydrides, active amides, active esters and active thioesters as mentioned for the reactive derivatives of compound [II]. The salt of the starting compound [IV] includes salts with inorganic acids or organic acids as mentioned for the salts of the cyclic amine

Preparation of salts or reactive derivatives of [III] and salts of [IV] and introduction of a protecting group into [III] or [IV] are easily performed by known processes or similar processes thereto. The reaction between compound [III] and compound [IV] is performed under the same reaction conditions (for example, presence or absence of condensation agent and kind thereof, kind of solvent, reaction temperature, reaction time, mol number of starting compounds) and treating conditions after the reaction (for example, for elimination of protecting group and purification) as mentioned for the reaction between compound [II] and cyclic amine

Compound [III] and compound [IV] are available by known methods or similar methods thereto.

Compound [I] has glutamate receptor inhibiting activity. Therefore, compound [I] is important for research on isolation, structure elucidation and local analysis of the glutamate receptor. Further, the compound is expected to be useful for elucidation of mechanism of memory and cranial nerve diseases with which glutamic acid is associated. Compound [I] has detoxication activity for such toxic metal ions as mercury and cadmium, since the compound is able to form a complex salt therewith as mentioned above. Glutamic receptor inhibiting action of the compound [I] is enhanced and duration time thereof is prolonged when the compound is in the form of a complex salt with cadmium or zinc.

REFERENCE EXAMPLE 1

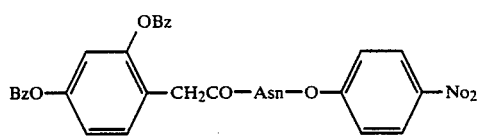

(wherein - Asn - is -

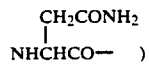

Preparation of 2,4-dibenzyloxyphenylacetyl-L-asparagine p-nitrophenyl ester [IIa-1]

(i) 2,4-Dihydroxybenzaldehyde [IV] (14.5 g) was dissolved in ethanol (60 ml) and then thereto were added benzyl chloride (30 ml) and sodium carbonate (1.7 g), followed by reflux under heating for 5 hours. Insoluble matters were removed by filtration. The filtrate was allowed to stand for cooling and then the produced solid was collected by filtration and recrystallized from ethanol to obtain 2,4-dibenzyloxybenzaldehyde [V] (20 g, yield 60%). Melting point: 89°–90° C.

(ii) 2,4-Dibenzyloxybenzaldehyde [V] (20 g) was dissolved in methanol (700 ml) and then, thereto was added sodium boronhydride (3.6 g) and this was left to stand at room temperature (20° C.) for 1.5 hours. To the reaction mixture was added water (1.5 liter) and the resulting precipitate was collected by filtration and recrystallized from ethanol to obtain 2,4-dibenzyloxybenzyl alcohol [VI] (19.8 g, yield 98%). Melting point: 84°–85° C.

(iii) 2,4-Dibenzyloxybenzyl alcohol [VI] (19.8 g) was dissolved in anhydrous benzene (150 ml) and then, thereto was added thionyl chloride (40 g), followed by reflux under heating for 1 hour. This was concentrated to dryness under reduced pressure to obtain crude 2,4-dibenzyloxybenzyl chloride [VII]. This was used for the subsequent reaction without purification.

(iv) The above obtained crude 2,4-dibenzyloxybenzyl chloride [VII] was dissolved in dimethyl sulfoxide (150 ml) and then thereto was added sodium cyanide (4 g), followed by stirring for 2 hours at room temperature (20° C.). The reaction mixture was added to water (1 liter) and extracted with dichloromethane (1 liter). The dichloromethane extract was concentrated under reduced pressure and the residue was purified by a silica gel column (inner diameter: 10 cm, length 50 cm; developer: dichloromethane-hexane 1:1 (v/v) mixed solution) and furthermore, was recrystallized from diethyl ether-hexane 2:1 (v/v) mixed solution to obtain 2,4-dibenzyloxyphenylacetonitrile [VIII] (14.3 g, yield from [VI]: 70%). Melting point: 99°–100° C.

(v) 2,4-Dibenzyloxyphenylacetonitrile [VIII] (14.3 g) was dissolved in ethanol (250 ml) and then, thereto was added an aqueous potassium hydroxide solution (prepared by dissolving 32 g of potassium hydroxide in 80 ml of water), followed by reflux under heating for 15 hours. The reaction mixture was concentrated under reduced pressure and then dissolved in water (100 ml). The solution was made acidic with concentrated hydrochloric acid and extracted with dichloromethane. The dichloromethane extract was dried over anhydrous magnesium sulfate and concentrated under reduced pressure. Thereafter, the residue was subjected to separation and purification by a silica gel column (inner diameter: 10 cm, length: 50 cm; developer: dichloromethane-ethyl acetate 4:1 (v/v) mixed solution). Thus separated and purified product was recrystallized from benzene to obtain 2,4-dibenzyloxyphenylacetic acid [IX] (14.4 g, yield 95%). Melting point: 139° C.

(vi) 2,4-Dibenzyloxyphenylacetic acid [IX] (1.4 g) was dissolved in anhydrous benzene (30 ml) and then thereto was added thionyl chloride (5 g) and the mixture was left to stand at room temperature (20° C.) for 20 minutes. The reaction mixture was concentrated to dryness under reduced pressure to obtain crude 2,4-dibenzyloxyphenylacetyl chloride [X]. This was used for the subsequent reaction without purification.

(vii) The above obtained crude 2,4-dibenzyloxyphenylacetyl chloride [X] was dissolved in anhydrous N,N-dimethylformamide (20 ml) and then thereto was added a solution of L-asparagine p-nitrophenyl ester trifluoroacetate in anhydrous N,N-dimethylformamide [prepared by treating N-(p-methoxybenzyloxycarbonyl)- L-asparagine p-nitrophenyl ester (1.6 g) with trifluoroacetic acid (3 ml) in the presence of anisole (1.2 g) at 0° C. for 1 hour, concentrating the treated product to dryness under reduced pressure and dissolving the residue in anhydrous N,N-dimethylformamide (20 ml)]. Thereto was further added triethylamine (1.8 ml), followed by concentrating under reduced pressure at 40° C. or lower. The residue was subjected to separation and purification by a silica gel column (inner diameter: 5 cm, length: 30 cm; developer: ethyl acetate) to obtain 2,4-dibenzyloxyphenylacetyl-L-asparagine p-nitrophenyl ester [IIa-1] (290 mg, yield from [IX] 13%).

REFERENCE EXAMPLE 2

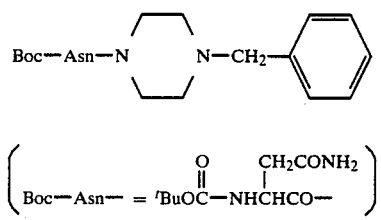

1-(N-tert-butoxycarbonyl-L-asparaginyl)-4-benzylpiperazine

1-Hydroxybenztriazole (4.63 g) and dicyclohexylcarbodimide (5.32 g) were added to a solution (200 ml) of N-tert-butoxycarbonyl-L-asparagine (6.0 g) in acetonitrile at room temperature, followed by stirring for 2 hours. Insoluble matters were removed by filtration and to the filtrate was added a solution (200 ml) of 1-benzylpiperazine (4.54 g) in acetonitrile, followed by stirring for 12 hours at room temperature. Insoluble matters were removed by filtration and the filtrate was concentrated and extracted with ethyl acetate. The ethyl acetate extract was washed with saturated aqueous sodium hydrogencarbonate solution and dried over anhydrous sodium sulfate. Then, the solvent was distilled off to obtain a colorless crystal 1-(N-tert-butoxycarbonyl-L-asparaginyl)-4-benzylpiperazine (11.3 g).

Melting point: 98°–100° C.
Elemental analysis for $C_{20}H_{30}N_4O_4$: Calcd. C: 61.52; H: 7.74; N: 14.35; Found C: 61.68; H: 7.63; N: 14.44.
IR spectrum $\nu_{max}$ (KBr)cm$^{-1}$: 3400, 3330 ($NH_2$), 1700, 1670, 1640 (C=O), 1620 (Ph).
NMR spectrum $\delta_{ppm}$ (CDCl$_3$): 1.43 (9H,s), 2.7–3.4 (4H, m), 3.5 (2H, s), 2.3–3.8 (6H, m), 4.96 (1H, m), 7.3 (5H, s).

REFERENCE EXAMPLE 3

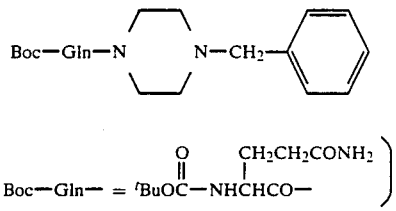

1-(N-tert-butoxycarbonyl-L-glutaminyl)-4-benzylpiperazine:

In the same manner as in Reference Example 2, N-tert-butoxycarbonyl-L-glutamine (8.0 g) and 1-benzylpiperazine (5.7 g) were condensed to obtain a colorless crystal 1-(N-tert-butoxycarbonyl-L-glutaminyl)-4-benzylpiperazine (11.2 g).

Melting point: 158°–159° C.
Elemental analysis for $C_{21}H_{32}N_4O_4$: Calcd. C: 62.35; H: 7.97; N: 13.85; Found C: 62.33; H: 8.05; N: 13.72.
IR spectrum $\nu_{max}$ (KBr)cm$^{-1}$: 3010, 2930 ($NH_2$), 1700, 1660, 1640 (C=O), 1600 (Ph).
NMR spectrum $\delta_{ppm}$ (CDCl$_3$): 1.43 (9H,s), 2.1–2.5 (4H, m), 3.43 (2H, s), 3.3–3.7 (8H, m), 4.57 (1H, m), 7.23 (5H, s).

REFERENCE EXAMPLE 4

1-(N-tert-butoxycarbonyl-L-asparaginyl)-4-phenylpiperazine

In the same manner as in Reference Example 2, N-tert-butoxycarbonyl-L-asparagine (4.3 g) and 1-phenylpiperazine (4.3 g) were condensed to obtain colorless powder 1-(N-tert-butoxycarbonyl-L-asparaginyl)-4-phenylpiperazine (9.5 g).

Mass spectrum: m/z=376 (M$^+$) ($C_{19}H_{28}N_4O_4$ M=376).
IR spectrum $\nu_{max}$ (KBr)cm$^{-1}$: 3300, 2950 ($NH_2$), 1700, 1640 (C=O), 1600 (Ph).
NMR spectrum $\delta_{ppm}$ (CDCl$_3$): 1.40 (9H, s), 1.9–3.4 (8H, m), 3.5–4.0 (2H, m), 5.00 (1H, m), 6.6–7,4 (5H, m).

REFERENCE EXAMPLE 5

1-(N-tert-butoxycarbonyl-L-glutaminyl)-4-phenylpiperazine

In the same manner as in Reference Example 2, N-tert-butoxycarbonyl-L-glutamine (4.7 g) and 1-phenylpiperazine were condensed to obtain colorless crystal 1-(N-tert-butoxycarbonyl-L-glutamine)-4-phenylpiperazine (7.4 g).

Melting point: 133°–135° C.

Elemental analysis for $C_{20}H_{30}N_4O_4$: Calcd. C: 61.52; H: 7.74; N: 14.35; Found C: 61.36; H: 7.80; N: 14.19.

IR spectrum $\nu_{max}$ (KBr)cm$^{-1}$: 3470, 3330 (NH$_2$), 1670, 1650 (C=O), 1610 (Ph).

NMR spectrum $\delta_{ppm}$ (CDCl$_3$), 1.43 (9H, s), 2.9–3.5 (8H, m), 3.4–3.9 (4H, m), 4.63 (1H, m), 6.7–7.4 (5H, m).

REFERENCE EXAMPLE 6

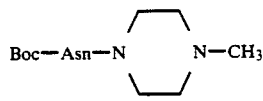

1-(N-tert-butoxycarbonyl-L-asparaginyl)-4-methylpiperazine:

In the same manner as in Reference Example 2, N-tert-butoxycarbonyl-L-asparagine (5.0 g) and 1-methylpiperazine (2.2 g) were condensed to obtain colorless crystal 1-(N-tert-butoxycarbonyl-L-asparaginyl)-4-methylpiperazine (5.5 g).

Melting point: 68°–70° C.

Elemental analysis for $C_{14}H_{26}N_4O_4$: Calcd. C: 53.48; H: 8.34; N: 17.82; Found C: 53.41; H: 8.49; N: 17.76.

IR spectrum $\nu_{max}$ (KBr)cm$^{-1}$: 3400 (NH$_2$), 1700, 1640 (C=O), 1610 (Ph).

NMR spectrum $\delta_{ppm}$ (CDCl$_3$): 1.43 (9H, s), 2.30 (3H, s), 2.2–2.7 (4H, m), 3.5–3.7 (6H, m), 5.00 (1H, m).

REFERENCE EXAMPLE 7

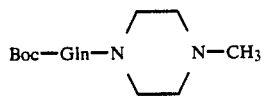

1-(N-tert-butoxycarbonyl-L-glutaminyl)-4-methylpiperazine:

In the same manner as in Reference Example 2, N-tert-butoxycarbonyl-L-glutamine and 1-methylpiperazine were condensed to obtain a crystal of 1-(N-tert-butoxycarbonyl-L-glutaminyl)-4-methylpiperazine (7.0 g).

Melting point: 209°–210° C.

Elemental analysis for $C_{15}H_{28}N_4O_4$: Calcd. C: 54.86; H: 8.59; N: 17.06; Found C: 55.03; H: 8.40; N: 16.83.

IR spectrum $\nu_{max}$ (KBr)cm$^{-1}$: 3350, 3200 (NH$_2$), 1700, 1680, 1640 (C=O), 1620 (Ph).

NMR spectrum $\delta_{ppm}$ (CDCl$_3$): 1.43 (9H, s), 2.3 (3H, s), 2.1–2.5 (4H, m), 3.3–3.7 (8H, m), 4.60 (1H, m).

REFERENCE EXAMPLE 8

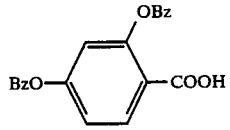

2,4-Dibenzyloxybenzoic acid (i) Potassium carbonate (3.3 g) and benzyl bromide (155 g) were added to a solution (300 ml) of 2,4-dihydroxybenzoic acid (38.9 g) in N,N-dimethylformamide, followed by stirring at 60° C. for 5 hours. Excess N,N-dimethylformamide was distilled off under reduced pressure and the residue was extracted with dichloromethane. The dichloromethane extract was washed with water and then dried over anhydrous sodium sulfate. Then the solvent was distilled off to obtain a colorless oily product, bynzyl 2,4-dibenzyloxybenzoate ester. This was used for the subsequent hydrolysis reaction without purification.

(ii) The benzyl ester obtained in the above (i) was dissolved in methanol (300 ml) and thereto was added potassium hydroxide (42.4 g), followed by stirring at 60° C. for 5 hours. After the reaction mixture was allowed to stand for cooling, excess methanol was distilled off. Water was added to the residue and then pH was adjusted to 3 with 5N hydrochloric acid. The precipitated crystal was collected by filtration, washed with water and dried. The crystal was recrystallized from dichloromethanemethanol (1:4) to obtain colorless needle-like 2,4-dibenzyloxybenzoic acid (65.6 g).

Melting point: 123°–124° C.

Elemental analysis for $C_{21}H_{18}O_4$: Calcd. C: 75.43; H: 5.43; Found C: 75.65; H: 5.42.

IR spectrum $\nu_{max}$ (KBr)cm$^{-1}$: 1720 (C=O), 1600 (Ph).

NMR spectrum $\delta_{ppm}$ (CDCl$_3$): 5.06 (2H, s), 5.16 (2H, s), 6.5–8.2 (13H, m).

REFERENCE EXAMPLE 9

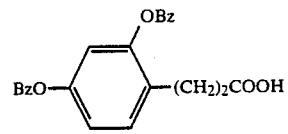

3-(2,4-Dibenzyloxyphenyl) propionic acid:

(i) Toluene (30 ml) was added to a mixture of 2,4-dibenzyloxybenzaldehyde (702 mg) and ethoxycarbonylmethylenetriphenylphosphoran (1.0 g), followed by stirring at 110° C. for 4 hours. The reaction mixture was concentrated under reduced pressure and the residue was purified by a silica gel column chromatography. From the fraction eluted with dichloromethane was obtained ethyl 3-(2,4-dibenzyloxyphenyl) acrylate (794 mg) (an oily product).

NMR spectrum $\delta_{ppm}$ (CDCl$_3$): 1.27 (3H, t), 4.20 (2H, q), 5.00 (2H, s), 5.08 (2H, s), 6.4–6.6 (3H, m), 7.1–7.5 (10H, m), 7.67–7.8 (1H, m), 7.86–8.05 (1H, m).

(ii) Sodium borohydride (10 mg) was added to an ethanolic solution (10 ml) of nickel chloride (100 mg), followed by stirring for 10 minutes. Then, thereto was added the ester obtained in the above (i) and sodium borohydride was added thereto little by little until the reaction terminated. Excess ethanol was distilled off and the residue was extracted with dichloromethane. The dichloromethane extract was washed with water and dried over anhydrous sodium sulfate and then the solvent was distilled off to yield oily ethyl 3-(2,4-dibenzyloxyphenyl) propionate ester (750 mg).

NMR spectrum $\delta_{ppm}$ (CDCl$_3$) 1.18 (3H, t), 2.45–3.05 (4H, m), 4.07 (2H, q), 4.97 (2H, s), 5.01 (2H, s), 6.3–7.5 (13H, m).

(iii) To an ethanolic solution (12.0 g, 300 ml) of the ester obtained in the above (ii) was added potassium hydroxide (10.3 g), followed by stirring at room temperature for 6 hours. Excess ethanol was distilled off and to the residue was added 5N hydrochloric acid to adjust pH to 3, resulting in precipitation of crystal. The crystal was collected by filtration, washed with water and dried and then recrystallized from dichloromethane-hexane (1:10) to obtain colorless needle-like crystal 3-(2,4-dibenzyloxyphenyl) propionic acid (9.4 g). Melting point: 125°-127° C.

Elemental analysis for $C_{23}H_{22}O_4$: Calcd. C: 76.22; H: 6.12; Found C: 76.26; H: 6.09.

IR spectrum $\nu$max (KBr)cm$^{-1}$: 1700 (C=O), 1610 (Ph).

NMR spectrum $\delta_{ppm}$ (CDCl$_3$): 2.4–3.1 (4H, m), 4.97 (2H, s), 5.02 (2H, s), 6.4–7.5 (13H, m).

EXAMPLE 1

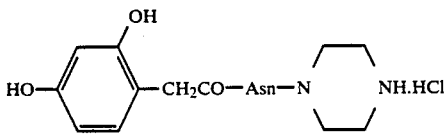

Preparation of 1-(2,4-dihydroxyphenylacetyl-L-asparaginyl) piperazine.hydrochloride [Ia]

2,4-Dibenzyloxyphenylacetyl-L-asparagine p-nitrophenyl ester [IIa-1] (90 mg) was dissolved in anhydrous N,N-dimethylformamide (0.5 ml) and thereto was added a solution (5 ml) of piperazine (58 mg) and 1-hydroxybenztriazole (6 mg) in anhydrous chloroform. The mixture was allowed to stand at room temperature for 2 hours and then the solvent was distilled off under reduced pressure. The residue was washed once with 4% aqueous sodium hydrogencarbonate solution and then thrice with water (5 ml). The resulting precipitate was dried and then dissolved in acetic acid (5 ml). The solution was subjected to catalytic reduction in the presence of 10% palladium-carbon (40 mg) for 3 hours in a hydrogen gas atmosphere. After the reaction, insoluble matters were removed by filtration and concentrated to dryness under reduced pressure. The residue was subjected to separation and purification by a high-performance liquid chromatography (reversed-phase partition column TSK gel ODS-120T manufactured by Toyo Soda Mfg., Co., Ltd.; inner diameter of the column: 46 mm, length: 250 mm; resin diameter: 5 μm; column temperature: 40° C.; eluent: mixed solvent of 0.03% hydrochloric acid and acetonitrile). The solvent was distilled off to yield 1-(2,4-dihydroxyphenylacetyl-L-asparaginyl) piperazine.hydrochloride [Ia] as white powder (40 mg, yield 47%).

Proton NMR of Ia (400 MHz, D$_2$O, ppm): 2.47 (dd, 1H), 2.63(dd, 1H), 2.95 and 3.03 (ddd-like, 1H each), 3.13 (m, 2H), 3.32 (s, 2H), 3.54 and 3.65 (ddd-like, 1H each), 3.73 (m, 2H), 4.95 (t, 1H), 6.27 (m, 2H), 6.98 (t-like, 1H).

EXAMPLE 2

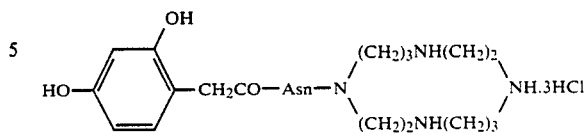

Preparation of 1-(2,4-dihydroxyphenylacetyl-L-asparaginyl)-1,4,8,11-tetraazacyclotetradecane.trihydrochloride [Ib]:

2,4-Dibenzyloxyphenylacetyl-L-asparagine p-nitrophenyl ester [IIa-1] (90 mg) was dissolved in anhydrous N,N-dimethylformamide (0.5 ml) and thereto was added a solution of 1,4,8,11-tetraazacyclotetradecane (134 mg) and 1-hydroxybenztriazole (6 mg) in anhydrous chloroform (5 ml). The mixture was allowed to stand at room temperature for 2 hours and then the solvent was distilled off under reduced pressure. The residue was washed once with 4% aqueous sodium hydrogencarbonate solution (5 ml) and then thrice with water (5 ml). The resulting precipitate was dried and then dissolved in acetic acid (5 ml). The solution was subjected to catalytic reduction in the presence of 10% palladium-carbon (40 mg) for 3 hours in a hydrogen gas atmosphere. After the reaction, insoluble matters were removed by filtration and the filtrate was concentrated to dryness under reduced pressure. The residue was subjected to separation and purification by a high-performance liquid chromatography (reversed-phase partition column TSK gel ODS-120T manufactured by Toyo Soda Mfg., Co., Ltd.; inner diameter of the column: 46 mm, length: 250 mm; resin diameter; 5 μm; column temperature: 40° C.; eluent: mixed solvent of 0.03% hydrochloric acid and acetonitrile). The solvent was distilled off to yield 1-(2,4-dihydroxyphenylacetyl-L-asparaginyl)-1,4,8,11-tetraazacyclotetradecane. trihydrochloride [Ib] as white powder (19 mg, yield 15%).

Proton NMR of Ib (400 MHz, D$_2$O, ppm): 1.94 and 2.02 (t-like, 2H each), 2.53 and 2.67 (dd, 1H each), 3.01 and 3.05 (t-like, 2H each), 3.18 and 3.19 (t-like, 2H each), 3.20 and 3.30 (dt-like, 1H each), 3.36 (dd-like, 2H), 3.43 (dd, 2H), 3.55 and 3.76 (ddd-like, 1H each), 4.80 (t, 1H), 6.29(m, 2H),6.92 (d-like, 1H)

EXAMPLE 3

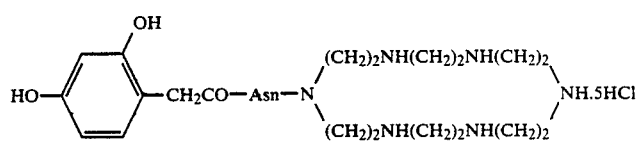

Preparation of 1-(2,4-dihydroxyphenylacetyl-L-asparaginyl)-1,4,7,10,13,16-hexaazacyclooctadecane.pentahydrochloride [Ic]:

2,4-Dibenzyloxyphenylacetyl-L-asparagine p-nitrophenyl ester [IIa-1] (90 mg) was dissolved in anhydrous N,N-dimethylformamide (0.5 ml) and thereto was added a solution of 1,4,7,10,13,16-hexaazacyclooctadecane (173 mg) and 1-hydroxybenztriazole (6 mg) in anhydrous chloroform (5 ml). The mixture was allowed to stand at room temperature for 2 hours and then the solvent was distilled off under reduced pressure. The residue was washed once with 4% aqueous sodium hydrogencarbonate solution (5 ml) and then thrice with water (5 ml). The resulting precipitate was dried and then dissolved in acetic acid (5 ml). The solution was subjected to catalytic reduction in the presence of 10% palladium-carbon (40 mg) for 3 hours in a hydrogen gas atmosphere. After the reaction, insoluble matters were removed by filtration and the filtrate was concentrated to dryness under reduced pressure. The residue was subjected to separation and purification by a high-performance liquid chromatography (reversed-phase partition column TSK gel ODS-120T manufactured by Toyo Soda Mfg., Co., Ltd.; inner diameter of the column: 46 mm, length: 250 mm; resin diameter: 5 μm; column temperature: 40° C.; eluent: mixed solvent of 0.03% hydrochloric acid and acetonitrile). The solvent was distilled off to obtain 1-(2,4-dihydroxyphenylacetyl-L-asparaginyl)-1,4,7,10,13,16-hexaazacyclooctadecane.pentahydrochloride [Ic] (14 mg, yield 9%).

Proton NMR of Ic (400 MHz, D$_2$O, ppm): 2.59 and 2.62 (dd, 1H each), 3.3–3.4 (s-like, 16H), 3.44 (t-like, 4H), 3.69 (t-like, 4H), 4.50 (t, 1H), 6.29 (m, 2H), 6.91(d-like, 1H).

EXAMPLE 4

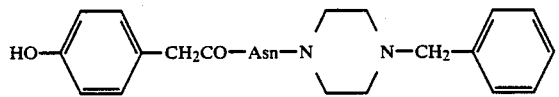

Preparation of
1-benzyl-4-(4-hydroxyphenylacetyl-L-asparaginyl)piperazine [Id]:

(i) 1-Benzyl-4-(L-asparaginyl)piperazine.dihydrochloride:

Tert-butyloxycarbonyl-1-asparagine (2.32 g) and 1-benzylpiperazine (1.74 ml) were dissolved in N,N-dimethylformamide (20 ml) and thereto were added 1-hydroxybenztriazole (1.35 g) and dicyclohexylcarbodiimide (2.27 g), followed by stirring at room temperature for 10 hours. The precipitate was removed by filtration and the solvent was distilled off under reduced pressure. The residual oily compound was dissolved in ethyl acetate (100 ml) and washed with a saturated aqueous sodium hydrogencarbonate solution and then with water and then was dried over anhydrous magnesium sulfate. The solvent was distilled off to obtain an oily compound, 1-benzyl-4-(tert-butyloxycarbonyl-L-asparaginyl)piperazine (2.8 g). Thereto was added trifluoroacetic acid (30 ml). The mixture was allowed to stand at room temperature for 30 minutes and thereafter thereto was added a solution (4 ml) of 6N hydrogen chloride in dioxane. Thereto was added ethyl ether (200 ml) to obtain 1-benzyl- 4-(L-asparaginyl)piperazine-dihydrochloride as a colorless solid (2.4 g) having a melting point of 159°–163° C.

Elemental analysis for C$_{15}$H$_{24}$Cl$_2$N$_4$O$_2$: Calcd. C: 49.59; H: 6.66; N: 15.42; Found C: 49.52; H: 6.58; N: 15.46.

(ii) 1-Benzyl-4-(4-hydroxyphenylacetyl-L-asparaginyl)piperazine:

4-Hydroxyphenylacetic acid (304 mg) and 1-benzyl-4-(L-asparaginyl)piperazine.dihydrochloride (726 mg) were dissolved in N,N-dimethylformamide (10 ml) and thereto were added 1-hydroxybenztriazole (270 mg), triethylamine (0.42 ml) and dicyclohexylcarbodiimide (470 mg), followed by stirring at room temperature for 15 hours. The resulting precipitate was removed by filtration and the solvent was distilled off under reduced pressure. To the residual oil was added acetonitrile (30 ml). After insoluble matters were again removed by filtration, the solvent was distilled off under reduced pressure. The oily residue was crystallized from a mixed solvent of ethyl acetate and diethyl ether, compound [Id] was obtained as a colorless solid (380 mg) having a melting point of 53°–54° C.

Elemental analysis for C$_{23}$H$_{28}$N$_4$O$_4$: Calcd. C: 65.08; H: 6.65; N: 13.20; Found C: 65.27; H: 6.73; N: 13.12.

EXAMPLE 5

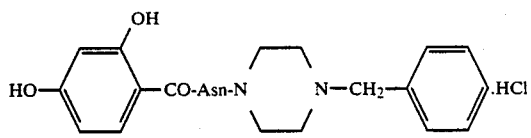

1-Benzyl-4-(2,4-dihydroxybenzoyl-L-asparaginyl) piperazine.hydrochloride:

(i) To a solution (20 ml) of 2,4-dibenzyloxybenzoic acid (712 mg) in acetonitrile were added 1-hydroxybenztriazole (459 mg) and dicyclohexylcarbodiimide (529 mg), followed by stirring at room temperature for 2 hours. The resulting urea was removed by filtration and the filtrate was concentrated to ½ in volume under reduced pressure.

Triethylamine (0.56 ml) was added to a solution (5 ml) in acetonitrile of 1-benzyl-4-L-asparaginyl) piperazine.dihydrochloride (1.02 g) obtained in Example 4 (i), followed by stirring at room temperature for 10 minutes. Thereto was added the acetonitrile solution obtained above, followed by stirring at room temperature for 6 hours. Reaction mixture was concentrated under reduced pressure and the residue was extracted with ethyl acetate. The ethyl acetate extract was washed with saturated aqueous sodium hydrogencarbonate solution and then with saturated aqueous sodium chloride solution. After drying over anhydrous sodium sulfate, the solvent was distilled off under reduced pressure to obtain a colorless oily product. To this product was added ether, followed by stirring to obtain a crystalline powder (1.29 g). This was purified by repowdering method with acetonitrile-ether to obtain colorless powder 1-benzyl-4-(2,4-dibenzyloxybenzoyl-L-asparaginyl)piperazine (1.03 g). Melting point: 66°–68° C.

Elemental analysis for C$_{36}$H$_{38}$N$_4$O$_5$: Calcd. C: 71.26; H: 6.31; N: 9.24; Found C: 71.40; H: 6.29; N: 9.06.

IR spectrum ν$_{max}$ (KBr)cm$^{-1}$: 3390 (NH$_2$), 1640 (C=O), 1600 (Ph).

NMR spectrum δ$_{ppm}$ (CDCl$_3$): 3.0–3.4 (6H, m), 3.6–3.8 (6H, m), 5.3–5.5 (1H, m), 6.5–8.8 (18H, m).

(ii) 3N-hydrochloric acid ethanol (0.5 ml) was added to ethanolic solution (20 ml) of 1-benzyl-4-(2,4-dibenzyloxybenzoyl-L-asparaginyl)piperazine (450 mg) obtained in the above (i). Then, the solution was subjected to catalytic reduction in the presence of 10% palladium-carbon (300 mg) for 3 hours at room temperature and normal pressure under hydrogen stream. The catalyst was removed by filtration and the filtrate was concentrated under reduced pressure to obtain a colorless oily product. Ether was added to the product, followed by stirring to obtain a crystalline powder. This was collected by filtration and dried to obtain 1-benzyl-4-(2,4-dihydroxybenzoyl-L-asparaginyl)piperazine.hydrochloride (225 mg).

Mass spectrum (SIMS): m/z=427 (M+ +H+) ($C_{22}H_{26}N_4O_5$: M=426).

Elemental analysis for $C_{22}H_{26}N_4O_5 \cdot HCl$: Calcd. C: 57.08; H: 5.88; N: 12.11; Found C: 56.83; H: 5.89; N: 11.86.

EXAMPLE 6

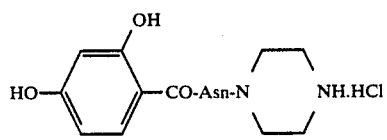

1-(2,4-Dihydroxybenzoyl-L-asparaginyl)piperazine.hydrochloride

Ethanolic solution (20 ml) of 1-benzyl-4-(2,4-dihydroxybenzoyl-L-asparaginyl)piperazine.hydrochloride (340 mg) was subjected to catalytic reduction in the presence of 10% palladium-carbon (300 mg) for 18 hours at room temperature and under atmospheric pressure in hydrogen stream. The catalyst was removed by filtration and the filtrate was concentrated under reduced pressure to obtain a colorless oily product. This product was powdered with addition of ether and then collected by filtration to obtain 1-(2,4-dihydroxybenzoyl-L-asparaginyl)piperazine.hydrochloride (212 mg).

Mass spectrum (SIMS): m/z=337 (M+ +H+) ($C_{15}H_{20}N_4O_5$: M=336).

Elemental analysis for $C_{15}H_{20}N_4O_5 \cdot HCl$: Calcd. C: 48.32; H: 5.68; N: 15.03; Found C: 48.53; H: 5.41; N: 15.19.

EXAMPLE 7

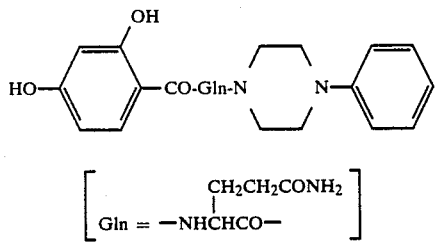

1-(2,4-Dihydroxybenzoyl-L-glutaminyl)-4-phenylpiperazine (i) To a solution (20 ml) of 2,4-dibenzyloxybenzoic acid (966 mg) in acetonitrile were added 1-hydroxybenztriazole (570 mg) and dicyclohexylcarbodiimide (656 mg), followed by stirring at room temperature for 2 hours. The resulting urea was removed by filtration and the filtrate was concentrated to ⅓ in volume under reduced pressure.

1-Phenyl-4-(N-tert-butoxycarbonyl-L-glutaminyl)piperazine (1.24 g) was dissolved in trifluoroacetic acid (5 ml), followed by stirring at room temperature for 30 minutes. To the reaction mixture was added toluene (20 ml) and the solvent was distilled off under reduced pressure. The residue was dissolved in acetonitrile (10 ml) and thereto was added triethylamine (0.89 ml) under ice cooling. To this solution was added the above concentrated solution, followed by stirring for 12 hours at room temperature. The reaction mixture was concentrated under reduced pressure and the residue was dissolved in ethyl acetate The ethyl acetate layer was washed with saturated aqueous sodium hydrogencarbonate solution and then with saturated aqueous sodium chloride solution The extract was dried over anhydrous sodium sulfate and then the solvent was distilled off. The residue was purified by a silica gel column chromatography. A crude crystal obtained from fraction eluted with 3% methanolic dichloromethane was recrystallized from ether-hexane (1:1) to obtain 1-(2,4-dibenzyloxybenzoyl-L-glutaminyl)-4-phenylpiperazine (451 mg). Melting point: 157°–158° C.

Elemental analysis for $C_{36}H_{38}N_4O_5$: Calcd. C: 71.26; H: 6.31; N: 9.24; Found C: 71.08; H: 6.40; N: 9.03.

IR spectrum $\nu_{max}$ (KBr)cm$^{-1}$: 3390 (NH$_2$), 1640 (C=O), 1600 (Ph).

NMR spectrum $\delta_{ppm}$ (CDCl$_3$): 2.3–2.7 (6H, m), 3.3–3.8 (6H, m), 5.03 (2H, s), 5.13 (2H, s), 5.2–6.0 (1H, m), 6.5–8.8 (18H, m).

(ii) 10% Palladium-carbon (120 mg) was added to an ethanolic solution (20 ml) of 1-(2,4-dibenzyloxybenzoyl-L-glutaminyl)-4-phenylpiperazine (364 mg) and catalytic reduction was carried out for 6 hours at room temperature and under atmospheric pressure in hydrogen stream. Thereafter, treatments were effected in the same manner as in Example 5 (ii) to obtain powdery 1-(2,4-dihydroxybenzoyl-L-glutaminyl)-4-phenylpiperazine (169 mg).

Mass spectrum (SIMS): m/z=427 (M+ +H+) ($C_{22}H_{26}N_4O_5$: M=426).

Elemental analysis for $C_{22}H_{26}N_4O_5$: Calcd. C: 61.96; H: 6.15; N: 13.14; Found C: 61.79; H: 6.33; N: 13.00.

EXAMPLE 8

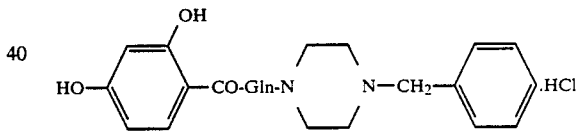

1-Benzyl-4-(2,4-dihydroxybenzoyl-L-glutaminyl)-piperazine.hydrochloride (i) Condensation of 1-benzyl-4-(N-tert-butoxycarbonyl-L-glutaminyl)piperazine (1.0 g) and 2,4-dibenzyloxybenzoic acid (752 mg) was carried out in the same manner as in Example 7 (i) to obtain colorless crystalline powder 1-benzyl-4-(2,4-dibenzyloxybenzoyl-L-glutaminyl)piperazine (375 mg). Melting point: 133°–135° C.

Elemental analysis for $C_{37}H_{40}N_4O_5$: Calcd. C: 71.59; H: 6.50; N: 9.03; Found C: 71.66; H: 6.39; N: 8.87.

IR spectrum $\nu_{max}$ (KBr)cm$^{-1}$: 3390 (NH$_2$), 1640 (C=O), 1600 (Ph).

NMR spectrum $\delta_{ppm}$ (CDCl$_3$): 1.8–2.6 (6H, m), 3.4–3.9 (8H, m), 4.4–4.5 (1H, m), 5.00 (2H, s), 5.20 (2H, s), 6.45–8.80 (18H, m).

(ii) 10% Palladium-carbon (75 mg) was added to an ethanolic solution (15 ml) of 1-benzyl-4-(2,4-dibenzyloxybenzoyl-L-glutaminyl)piperazine (136 mg) and partial catalytic reduction was carried out in the same manner as in Example 5 (ii) to obtain 1-benzyl-4-(2,4-dihydroxybenzoyl-L-glutaminyl)piperazine.hydrochloride (79 mg) as a powder.

Mass spectrum (SIMS): m/z=441 (M++H+) (C23H28N4O5: M=440).

Elemental analysis for C23H28N4O5.HCl: Calcd. C: 57.92; H: 6.13; N: 11.75; Found C: 58.11; H: 5.98; N: 11.70.

EXAMPLE 9

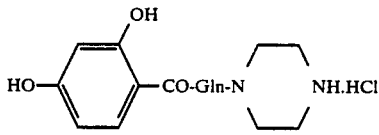

1-(2,4-Dihydroxybenzoyl-L-glutaminyl)piperazine.hydrochloride

10% Palladium-carbon (150 mg) was added to an ethanolic solution (15 ml) of 1-benzyl-4-(2,4-dihydroxybenzoyl-L-glutaminyl)piperazine.hydrochloride (276 mg) obtained in Example 8 (ii) and catalytic reduction was carried out in the same manner as in Example 6 to obtain colorless powder 1-(2,4-dihydroxybenzoyl-L-glutaminyl)piperazine.hydrochloride (183 mg).

Mass spectrum (SIMS) m/z=351 (M++H+) (C16H22N4O5: M=350).

Elemental analysis for C16H22N4O5.HCl: Calcd. C: 49.68; H: 5.99; N: 14.49; Found C: 49.46; H: 6.11; N: 14.27.

EXAMPLE 10

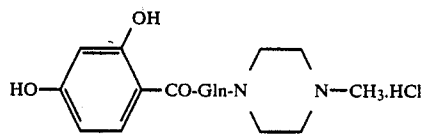

1-(2,4-Dihydroxybenzoyl-L-glutaminyl)-4-methylpiperazine.hydrochloride (i) Condensation of 1-methyl-4-(N-tert-butoxycarbonyl-L-glutaminyl)piperazine (926 mg) and 2,4-dibenzyloxybenzoic acid (1.1 g) was carried out in the same manner as in Example 7 (i) to obtain colorless powder 1-(2,4-dibenzyloxybenzoyl-L-glutaminyl)-4-methylpiperazine.hydrochloride (321 mg). Melting point: 64°-66° C.

Elemental analysis for C31H38N4O5: Calcd. C: 68.36; H: 6.66; N: 10.29; Found C: 68.31; H: 6.57; N: 10.43.

IR spectrum νmax (KBr)cm−1: 3300 (NH2), 1640 (C=O), 1600 (Ph).

NMR spectrum δppm (CDCl3): 2.26 (3H, s), 1.9–2.6 (4H, m), 3.3–3.7 (6H, m), 5.03 (2H, s), 5.20 (2H, s), 5.3–5.6 (1H, m), 6.5–8.8 (13H, m).

(ii) 10% Palladium-carbon (200 mg) was added to an ethanolic solution (50 ml) of 1-(2,4-dibenzyloxybenzoyl-L-glutaminyl)-4-methylpiperazine.hydrochloride (270 mg) obtained above and catalytic reduction was carried out at room temperature and under atmospheric pressure in hydrogen stream. Thereafter, treatments were conducted in the same manner as in Example 5 (ii) to obtain colorless crystalline powder 1-(2,4-dihydroxybenzoyl-L-glutaminyl)-4-methylpiperazine.hydrochloride (160 mg). Melting point: 144°-145° C.

Mass spectrum (SIMS) m/z=365 (M++H+) (C17H24N4O5: M=364).

Elemental analysis for C17H24N4O5.HCl: Calcd. C: 50.93; H: 6.29; N: 13.98; Found C: 50.82; H: 6.11; N: 13.76.

EXAMPLE 11

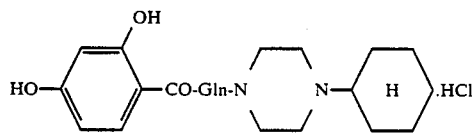

1-(2,4-Dihydroxybenzoyl-L-glutaminyl)-4-cyclohexylpiperazine.hydrochloride 3N-hydrochloric acid ethanol (0.2 ml) was added to an ethanolic solution of 1-(2,4-dihydroxybenzoyl-L-piperazine (87 mg) obtained in Example 7 (ii) and then thereto was added 10% palladium-carbon (65 mg) and catalytic reduction was conducted for 24 hours at 40° C. and under atmospheric pressure in hydrogen stream. Thereafter, treatments were effected in the same manner as in Example 5 (ii) to obtain colorless powder 1-(2,4-dihydroxybenzoly-L-glutaminyl)- 4-cyclohexylpiperazine.hydrochloride (72 mg).

Mass spectrum (SIMS): m/z=433 (M++H+) (C22H32N4O5: M=432).

Elemental analysis for C22H32N4O5.HCl: Calcd. C: 56.34; H: 7.09; N: 11.95; Found C: 56.42; H: 7.16; N: 12.17.

EXAMPLE 12

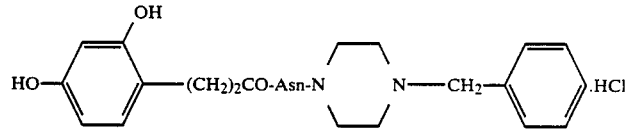

1-Benzyl-4-[3-(2,4-dihydroxyphenyl)propionyl-L-asparaginyl]piperazine.hydrochloride (i) To a solution (30 ml) of 3-(2,4-dibenzyloxyphenyl)propionic acid (802 mg) in acetonitrile were added 1-hydroxybenztriazole (465 mg) and dicyclohexylcarbodiimide (530 mg) at room temperature, followed by stirring for 2 hours at room temperature. The resulting urea was removed by filtration and the filtrate was concentrated to ⅓ in volume under reduced pressure A solution (5 ml) of 1-benzyl-4-(N-tert-butoxycarbonyl-L-asparaginyl)piperazine (1.0 g) in trifluoroacetic acid was stirred at room temperature for 30 minutes. Thereafter, treatments were made in the same manner as in Example 7 (i) to obtain a crude product This was recrystallized from ether to obtain colorless needle-like crystal 1-benzyl-4-[3-(2,4-dibenzyloxyphenyl) propionyl-L-asparaginyl]piperazine (794 mg). Melting point: 112°-114° C.

Elemental analysis for C38H42N4O5: Calcd. C: 71.90; H: 6.67; N: 8.83; Found C: 71.92; H: 6.53; N: 8.66.

IR spectrum $\nu_{max}$ (KBr)cm$^{-1}$: 3400, 3330 (NH$_2$), 1660 (C=O), 1620 (Ph).

NMR spectrum $\delta_{ppm}$ (CDCl$_3$): 1.5–2.2 (4H, m), 2.2–2.7 (6H, m), 2.80–3.03 (2H, m), 3.33–3.70 (4H, m), 4.10 (1H, m), 5.00 (2H, s), 5.06 (2H, s), 6.4–7.5 (15H, m).

(ii) 10% Palladium-carbon (120 mg) and 3N-hydrochloric acid ethanol (0.2 ml) were added to an ethanolic solution (20 ml) of 1-benzyl-4-[3-(2,4-dibenzyloxyphenyl)propionyl-L-asparaginyl]piperazine (413 mg) obtained above and in the same manner as in Example 5 (ii) catalytic reduction was carried out at room temperature and atmospheric pressure to obtain colorless crystalline powder 1-benzyl-4-[3-(2,4-dihydroxyphenyl)propionyl-L-asparaginyl]piperazine.hydrochloride (204 mg).

Mass spectrum (SIMS): m/z=455 (M$^+$+H$^+$) (C$_{24}$H$_{30}$N$_4$O$_5$: M=454).

Elemental analysis for C$_{24}$H$_{30}$N$_4$O$_5$.HCl: Calcd. C: 58.71; H: 6.36; N: 11.41; Found C: 58.89; H: 6.30; N: 11.27.

EXAMPLE 13

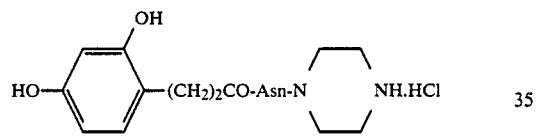

1-[3-(2,4-dihydroxyphenyl)propionyl-L-asparaginyl]-piperazine.hydrochloride

1-Benzyl-4-[3-(2,4-dihydroxyphenyl)propionyl-L-asparaginyl]piperazine.hydrochloride (76 mg) obtained in Example 12 was subjected to catalytic reduction in the same manner as in Example 6 to obtain crystalline powder 1-[3-(2,4-dihydroxyphenyl)propionyl-L-asparaginyl]piperazine.hydrochloride (49 mg).

Mass spectrum (SIMS): m/z=365 (M$^+$+H$^+$) (C$_{17}$H$_{24}$N$_4$O$_5$: M=364).

Elemental analysis for C$_{17}$H$_{24}$N$_4$O$_5$.HCl: Calcd. C: 50.93; H: 6.29; N: 13.98; Found C: 51.07; H: 6.27; N: 13.72.

EXAMPLE 14

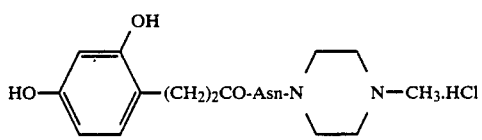

1-[3-(2,4-dihydroxyphenyl)propionyl-L-asparaginyl]-4-methylpiperazine.hydrochloride (i) Condensation of 3-(2,4-dibenzyloxyphenyl) propionic acid (961 mg) and 1-(N-tert-butoxycarbonyl-L-asparaginyl)-4-methylpiperazine (1.0 g) was carried out in the same manner as in Example 12 (i) to obtain colorless crystalline 1-[3-(2,4-dibenzyloxyphenyl) propionyl-L-asparaginyl]-4-methylpiperazine (1.39 mg). Melting point: 121°–123° C.

Elemental analysis for C$_{32}$H$_{38}$N$_4$O$_5$: Calcd. C: 68.79; H: 6.86; N: 10.03; Found C: 68.56; H: 6.72; N: 9.82.

IR spectrum $\nu_{max}$ (KBr)cm$^{-1}$: 3300 (NH$_2$), 1670, 1640 (C=O), 1600 (Ph).

NMR spectrum $\delta_{ppm}$ (CDCl$_3$): 1.50–2.06 (4H, m), 2.06 (3H, s), 2.16–2.66 (6H, m), 2.76–3.10 (2H, m), 3.33–3.83 (2H, m), 4.1 (1H, m), 5.00 (2H, s), 5.03 (2H, s), 6.4–7.5 (13H, m).

(ii) 1-[3-(2,4-dibenzyloxyphenyl)propionyl-L-asparaginyl]-4-methylpiperazine (500 mg) obtained above was subjected to catalytic reduction in the same manner as in Example 6 to obtain colorless crystalline powder 1-[3-(2,4-dihydroxyphenyl)propionyl-L-asparaginyl]-4-methylpiperazine hydrochloride (330 mg). Melting point: 144°–145° C.

Mass spectrum (SIMS): m/z=397 (M$^+$+H$^+$) (C$_{18}$H$_{26}$N$_4$O$_5$: M=378).

Elemental analysis for C$_{18}$H$_{26}$N$_4$P$_5$.HCl: Calcd. C: 52.11; H: 6.56; N: 13.51; Found C: 52.16; H: 6.29; N: 13.68.

EXAMPLE 15

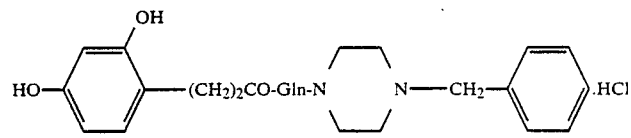

1-[3-(2,4-Dihydroxyphenyl)propionyl-L-glutaminyl]-4-benzylpierazine.hydrochloride (i) Condensation of 3-(2,4-dibenzyloxyphenyl) propionic acid (748 mg) and 1-benzyl-4-(N-tert-butoxycarbonyl-L-glutaminyl)piperazine (1.0 g) was effected in the same manner as in Example 8 (i) to obtain colorless crystalline powder 1-[3-(2,4-dibenzyloxyphenyl)propionyl-L-glutaminyl]-4-benzylpiperazine (1.20 g). Melting point: 145°–147° C.

Elemental analysis for C$_{39}$H$_{44}$N$_4$O$_5$: Calcd. C: 72.20; H: 6.84; N: 8.64; Found C: 72.01; H: 6.77; N: 8.50.

IR spectrum $\nu_{max}$ (KBr)cm$^{-1}$: 3450 (NH$_2$), 1680, 1660 (C=O), 1600 (Ph).

NMR spectrum $\delta_{ppm}$ (CDCl$_3$): 1.6–2.2 (4H, m), 2.2–2.6 (6H, m), 2.8–3.0 (2H, m), 3.3–3.6 (6H, m), 4.76 (1H. m), 4.96 (2H, s), 5.03 (2H, s), 6.3–7.4 (18H, m).

(ii) An ethanolic solution (20 ml) of 1-[3-(2,4-dibenzyloxyphenyl)propionyl-L-glutaminyl]-4-benzylpiperazine (336 mg) obtained above was subjected to catalytic reduction in the same manner as in Example 5 (ii) to obtain crystalline powder 1-[3-(2,4-dihydroxyphenyl)-propionyl-L-glutaminyl]-4-benzylpiperazine hydrochloride (192 mg).

Mass spectrum (SIMS): m/z=469 (M$^+$+H$^+$) (C$_{25}$H$_{32}$N$_4$O$_5$: M=468).

Elemental analysis for C$_{25}$H$_{32}$N$_4$O$_5$.HCl: Calcd. C: 59.45; H: 6.59; N: 11.10; Found C: 59.50; H: 6.38; N: 10.92.

EXAMPLE 16

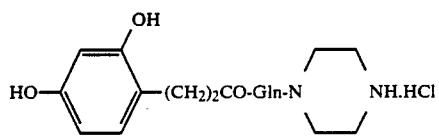

1-3-(2,4-Dihydroxyphenyl)propionyl-L-glutaminyl]-piperazine.hydrochloride

An ethanolic solution (16 ml) of 1-[3-(2,4-dihydroxyphenyl)propionyl-L-glutaminyl]-4-benzylpiperazine.hydrochloride (56 mg) obtained in Example 15 (ii) was subjected to catalytic reduction in the same manner as in Example 6 to obtain powder (34 mg) of 1-[3-(2,4-dihydroxyphenyl)propionyl-L-glutaminyl]piperazine.hydrochloride.

Mass spectrum (SIMS): m/z=379 (M$^+$+H$^+$) ($C_{18}H_{26}N_4O_5$: M=378.

Elemental analysis for $C_{18}H_{26}N_4O_5$.HCl: Calcd. C: 52.11; H: 6.56; N: 13.51; Found C: 51.93; H: 6.60; N: 13.29.

EXAMPLE 17

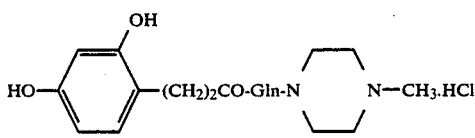

1-[3-(2,4-Dihydroxyphenyl)propionyl-L-glutaminyl]-4-methylpiperazine.hydrochloride (i) Condensation of 3-(2,4-dibenzyloxyphenyl) propionic acid (1.0 g) and 1-(N-tert-butoxycarbonyl-L-asparaginyl)-4-methylpiperazine (1.0 g) was carried out in the same manner as in Example 12 (i) to obtain colorless crystal 1-[3-(2,4-dibenzyloxyphenyl) propionyl-L-glutaminyl]-4-methylpiperazine (1.11 g). Melting point: 120°-122° C.

Elemental analysis for $C_{33}H_{40}N_4O_5$: Calcd. C: 69.21; H: 7.04; N: 9.78; Found C: 69.04; H: 6.88; N: 9.66.

IR spectrum $\nu_{max}$ (KBr)cm$^{-1}$: 3450 (NH$_2$), 1740, 1640 (C=O), 1600 (Ph).

NMR spectrum $\delta_{ppm}$ (CDCl$_3$): 1.5-2.1 (4H, m), 2.26 (3H, s), 2.2-2.6 (6H, m), 2.7-3.1 (2H, m), 3.2-3.8 (4H, m), 5.00 (2H, s), 5.06 (2H, s), 6.4-7.5 (13H, m).

(ii) An ethanolic solution (20 ml) of 1-[3-(2,4-dibenzyloxyphenyl)propionyl-L-glutaminyl]-4-methylpiperazine (360 mg) obtained above was subjected to catalytic reduction in the same manner as in Example 6 to obtain colorless powder 1-[3-(2,4-dihydroxyphenyl)-propionyl-L-glutaminyl]-4-methylpiperazine.hydrochloride (246 mg). Melting point: 135°-137° C.

Mass spectrum (SIMS): m/z=393 (M$^+$+H$^+$) ($C_{19}H_{28}N_4O_5$: M=392).

Elemental analysis for $C_{19}H_{28}N_4O_5$.HCl: Calcd. C: 53.20; H: 6.81; N: 13.07; Found C: 53.21; H: 6.77; N: 13.19.

EXAMPLE 18

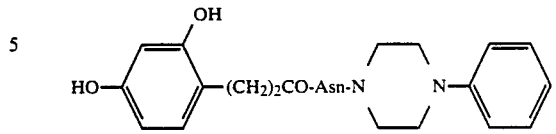

1-[3-(2,4-Dihydroxyphenyl)propionyl-L-asparaginyl-4-phenylpiperazine (i) Condensation of 3-(2,4-dibenzyloxyphenyl)propionic acid (772 mg) and 1-(N-tert-butoxycarbonyl-L-asparaginyl)-4-phenylpiperazine (964 mg) was carried out in the same manner as in Example 7 (i) to obtain colorless crystal 1-[3-(2,4-dibenzyloxyphenyl)propionyl-L-asparaginyl]- 4-phenylpiperazine (430 mg). Melting point: 96°-98° C.

Elemental analysis for $C_{37}H_{40}N_4O_5$: Calcd. C: 71.59; H: 6.50; N: 9.03; Found C: 71.37; H: 6.70; N: 9.11.

IR spectrum $\nu_{max}$ (KBr)cm$^{-1}$: 3400, 3300 (NH$_2$), 1660, 1640 (C=O), 1600 (Ph).

NMR spectrum $\delta_{ppm}$ (CDCl$_3$): 2.0-3.3 (12H, m), 3.5-3.8 (2H, m), 4.93 (2H, s), 5.00 (2H, s), 5.12 (1H, m), 6.3-7.5 (18H, m).

(ii) An ethanolic solution (20 ml) of 1-[3-(2,4-dibenzyloxyphenyl)propionyl-L-asparaginyl]-4-phenylpiperazine (130 mg) obtained above was subjected to catalytic reduction in the same manner as in Example 7 (ii) to obtain powdery 1-[3-(2,4-dihydroxyphenyl) propionyl-L-asparaginyl]-4-phenylpiperazine (74 mg).

Mass spectrum (SIMS): m/z=441 (M$^+$+H$^-$) ($C_{23}H_{28}N_4O_5$: M=440).

Elemental analysis for $C_{23}H_{28}N_4O_5$: Calcd. C: 62.71; H: 6.41; N: 12.72; Found C: 62.46; H: 6.45; N: 12.46.

EXAMPLE 19

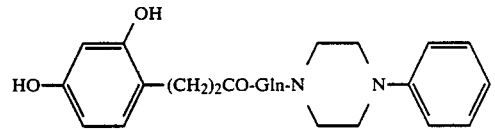

1-[3-(2,4-Dihydroxyphenyl)propionyl-L-glutaminyl]-4-phenylpiperazine (i) Condensation of 3-(2,4-dibenzyloxyphenyl)propionic acid (772 mg) and 1-(N-tert-butoxycarbonyl-L-glutaminyl)-4-phenylpiperazine (1.0 g) was carried out in the same manner as in Example 7 (i) to obtain colorless crystal 1-[3-(2,4-dibenzyloxyphenyl) propionyl-L-glutaminyl]-4-phenylpiperazine (762 mg). Melting point: 118°-120° C.

Elemental analysis for $C_{38}H_{42}N_4O_5$: Calcd. C: 71.90; H: 6.67; N: 8.83; Found C: 72.10; H: 6.56; N: 8.77.

IR spectrum $\nu_{max}$ (KBr)cm$^{-1}$: 3350 (NH$_2$), 1680, 1660 (C=O), 1600 (Ph).

NMR spectrum $\delta_{ppm}$ (CDCl$_3$): 1.5-2.3 (4H, m), 2.4-3.1 (4H, m), 3.1-3.3 (4H, m), 3.5-3.8 (4H, m), 4.86 (1H, m), 5.00 (2H, s), 5.06 (2H, s), 6.4-7.6 (18H, m).

(ii) An ethanolic solution (20 ml) of 1-[3-(2,4-dibenzyloxyphenyl)propionyl-L-glutaminyl]-4-phenylpiperazine (316 mg) obtained above was subjected to catalytic reduction in the same manner as in Example 7 (ii) to obtain crystalline powder 1-[3-(2,4-dihydroxyphenyl)-propionyl]-4-phenylpiperazine (202 mg).

Mass spectrum (SIMS): m/z=455 (M+ +H+) (C24H30N4O5: M=454).

Elemental analysis for C24H30N4O5: Calcd. C: 63.42; H: 6.65; N: 12.33; Found C: 63.60; H: 6.61; N: 12.22.

EXAMPLE 20

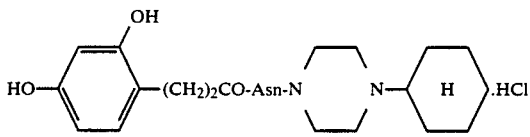

1-[3-(2,4-dihydroxyphenyl)propionyl-L-asparaginyl]-4-cyclohexylpiperazine.hydrochloride An ethanolic solution (20 ml) of 1-[3-(2,4-dihydroxyphenyl)propionyl-L-asparaginyl]-4-phenylpiperazine (110 mg) obtained in Example 18 (ii) was subjected to catalytic reduction in the same manner as in Example 11 to obtain 1-[3-(2,4-dihydroxyphenyl) propionyl-L-asparaginyl]-4-cyclohexylpiperazine.hydrochloride (86 mg).

Mass spectrum (SIMS): m/z=447 (M+ +H+) (C23H34N4O5: M=446).

Elemental analysis for C23H34N4O5.HCl: Calcd. C: 57.19; H: 7.30; N: 11.60; Found C: 57.04; H: 7.29; N: 11.49.

EXAMPLE 21

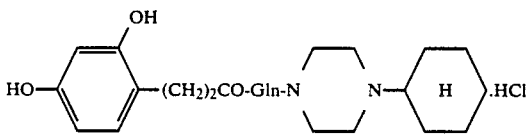

1-[3-(2,4-dihydroxyphenyl)propionyl-L-glutaminyl]-4-cyclohexylpiperazine.hydrochloride 1-[3-(2,4-Dihydroxyphenyl)propionyl-L-glutaminyl]-4-phenylpiperazine (172 mg) obtained in Example 19 (ii) was subjected to catalytic reduction in the same manner as in Example 11 to obtain powdery 1-[3-(2,4-dihydroxyphenyl)propionyl-L-glutaminyl]-4-cyclohexylpiperazine.hydrochloride (109 mg).

Mass spectrum (SIMS): m/z=461 (M+ +H+) (C24H36N4O5: M=460).

Elemental analysis for C24H36N4O5.HCl: Calcd. C: 57.99; H: 7.50; N: 11.28; Found C: 57.72; H: 7.62; N: 10.99.

EXAMPLE 22

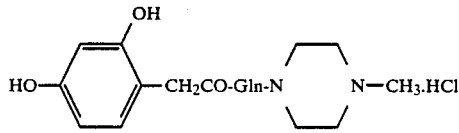

1-(2,4-Dihydroxyphenylacetyl-L-glutaminyl)-4-methylpiperazine.hydrochloride (i) Condensation of 2,4-dibenzyloxyphenylacetic acid (1.0 g) and 1-(N-tert-butoxycarbonyl-L-glutaminyl)-4-methoxypiperazine (966 mg) was carried out in the same manner as in Example 12 (i) to obtain colorless crystal 1-(2,4-dibenzyloxyphenylacetyl-L-glutaminyl)-4-methylpiperazine (1.0 g). Melting point: 127°-128° C.

Elemental analysis for C32H38N4O5: Calcd. C: 68.79; H: 6.86; N: 10.03; Found C: 68.77; H: 6.83; N: 9.95.

IR spectrum $\nu_{max}$ (KBr)cm$^{-1}$: 3400 (NH2), 1660 (C=O), 1600 (Ph).

NMR spectrum $\delta_{ppm}$ (CDCl3): 1.5-2.5 (8H, m), 2.23 (3H, s), 3.3-3.7 (6H, m), 5.00 (2H, s), 5.03 (2H, s), 6.5-7.5 (13H, m).

(ii) 1-(2,4-Dibenzyloxyphenylacetyl-L-glutaminyl)-4-methylpiperazine (350 mg) obtained above was subjected to catalytic reduction in the same manner as in Example 6 to obtain 1-(2,4-dihydroxyphenylacetyl-L-glutaminyl)-4-methylpiperazine.hydrochloride (240 mg). Melting point: 130°-131° C.

Elemental analysis for C18H26N4O5.HCl: Calcd. C: 52.11; H: 6.56; N: 13.51; Found C: 52.07; H: 6.73; N: 13.28.

Mass spectrum (SIMS): m/z=379 (M+ +H+) (C19H28N4O5: M=378).

EXAMPLE 23

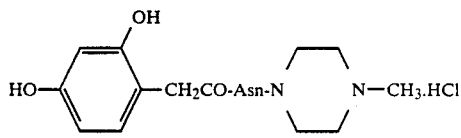

1-(2,4-Dihydroxyphenylacetyl-L-asparaginyl)-4-methylpiperazine.hydrochloride (i) Condensation of 2,4-dibenzyloxyphenylacetic acid (923 mg) and 1-(N-tert-butoxycarbonyl-L-asparaginyl)-4-methylpiperazine (1.0 g) was carried out in the same manner as in Example 12 (i) to obtain colorless crystalline powder 1-(2,4-dibenzyloxyphenyl-L-asparaginyl)-4-methylpiperazine (1.18 g). Melting point: 83°-85° C.

Elemental analysis for C31H36N4O5: Calcd. C: 68.36; H: 6.66; N: 10.29; Found C: 68.19; H: 6.73; N: 10.03.

IR spectrum $\nu_{max}$ (KBr)cm$^{-1}$: 3300 (NH2), 1740, 1660 (C=O), 1620 (Ph).

NMR spectrum $\delta_{ppm}$ (CDCl3): 1.5-2.5 (8H, m), 2.26 (3H, s), 3.3-3.7 (4H, m), 4.10 (1H, m), 5.03 (2H, s), 5.06 (2H, s), 6.4-7.5 (13H, m).

(ii) 1-(2,4-Dibenzyloxyphenylacetyl-L-asparaginyl)-4-methylpiperazine (500 mg) obtained above was subjected to catalytic reduction in the same manner as in Example 6 to obtain colorless crystalline powder (326 mg) of 1-(2,4-dihydroxyphenylacetyl-L-asparaginyl)-4-methylpiperazine.hydrochrolide (326 mg). Melting point: 154°-156° C.

Elemental analysis for C17H24N4O5.HCl: Calcd. C: 50.93; H: 6.29; N: 13.98; Found C: 50.72; H: 6.35; N: 14.02.

Mass spectrum (SIMS): m/z=365 (M+ +H+) (C17H24N4O5: M=364).

EXAMPLE 24

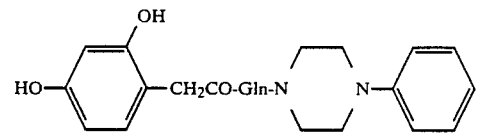

1-(2,4-Dihydroxyphenylacetyl-L-glutaminyl)-4-phenylpiperazine (i) Condensation of 2,4-dibenzyloxyphenylacetic acid (742 mg) and 1-(N-tert-butoxycarbonyl-L-glutaminyl)-4-phenylpiperazine (1.0 g) was carried out in the same manner as in Example 12 (i) to obtain 1-(2,4-dibenzyloxyphenylacetyl-L-glutaminyl)-4-phenylpiperazine (923 mg). Melting point: 86°–88° C.

Elemental analysis for $C_{37}H_{40}N_4O_5$: Calcd. C: 71.59; H: 6.50; N: 9.03; Found C: 71.42; H: 6.64; N: 8.87.

IR spectrum $\nu_{max}$ (KBr) $cm^{-1}$: 3300 ($NH_2$), 1650, 1630 (C=O), 1600 (Ph).

NMR spectrum $\delta_{ppm}$ ($CDCl_3$): 1.5–2.2 (4H, m), 3.0–3.3 (4H, m), 3.5–3.8 (6H, m), 4.86 (1H, m), 5.03 (2H, s), 5.06 (2H, s), 6.5–7.5 (18H, m).

(ii) 1-(2,4-Dibenzyloxyphenylacetyl-L-glutaminyl)-4-phenylpiperazine (436 mg) obtained above was subjected to catalytic reduction in the same manner as in Example 7 (ii) to obtain powder of 1-(2,4-dihydroxyphenylacetyl-L-glutaminyl)-4-phenylpiperazine (219 mg).

Mass spectrum (SIMS): m/z=441 ($M^+ + H^+$) ($C_{23}H_{28}N_4O_5$: M=440).

Elemental analysis for $C_{23}H_{28}N_4O_5$: Calcd. C: 62.71; H: 6.41; N: 12.72; Found C: 62.93; H: 6.44; N: 12.58.

EXAMPLE 25

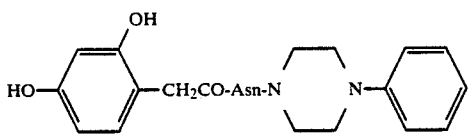

1-(2,4-Dihydroxyphenylacetyl-L-asparaginyl)-4-phenylpiperazine (i) Condensation of 2,4-dibenzyloxyphenylacetic acid (771 mg) and 1-(N-tert-butoxycarbonyl-L-asparaginyl)-4-phenylpiperazine (1.0 g) was carried out in the same manner as in Example 12 (i) to obtain crystal of 1-(2,4-dibenzyloxyphenylacetyl-L-asparaginyl)-4-phenylpiperazine (1.13 g). Melting point: 94°–96° C.

Elemental analysis for $C_{36}H_{38}N_4O_5$: Calcd. C: 71.26; H: 6.31; N: 9.24; Found C: 71.48; H: 6.44; N: 9.22.

IR spectrum $\nu_{max}$ (KBr)$cm^{-1}$: 3300 ($NH_2$), 1660, 1640 (C=O), 1600 (Ph).

NMR spectrum $\delta_{ppm}$ ($CDCl_3$): 1.5–2.3 (4H, m), 2.7–3.2 (4H, m), 3.4–3.7 (4H, m), 4.96 (2H, s), 5.03 (2H, s), 5.12 (1H, m), 6.4–7.5 (18H, m).

(ii) 1-(2,4-Dibenzyloxyphenylacetyl-L-asparaginyl)-4-phenylpiperazine (636 mg) obtained above was subjected to catalytic reduction in the same manner as in Example 7 (ii) to obtain crystalline powder of 1-(2,4-dihydroxyphenylacetyl-L-asparaginyl)-4-phenylpiperazine (402 mg).

Mass spectrum (SIMS): m/z=427 ($M^+ + H^+$) ($C_{22}H_{26}N_4O_5$: M=426).

Elemental analysis for $C_{22}H_{26}N_4O_5$: Calcd. C: 61.96; H: 6.15; N: 13.14; Found C: 61.88; H: 6.17; N: 12.93.

EXAMPLE 26

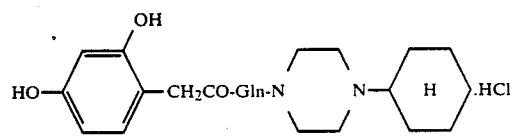

1-(2,4-Dihydroxyphenylacetyl-glutaminyl)-4-cyclohexylpiperazine.hydrochloride 1-(2,4-Dihydroxyphenylacetyl-L-glutaminyl)-4-phenylpiperazine (161 mg) obtained in Example 24 was subjected to catalytic reduction in the same manner as in Example 11 to obtain 1-(2,4-dihydroxyphenylacetyl-L-glutaminyl-4-cyclohexylpiperazine.hydrochloride (144 mg).

Mass spectrum (SIMS): m/z=447 ($M^+ + H^+$) ($C_{23}H_{34}N_4O_5$: M=446).

Elemental analysis for $C_{23}H_{34}N_4O_5 \cdot HCl$: Calcd. C: 57.19; H: 7.30; N: 11.60; Found C: 57.08; H: 7.46; N: 11.78.

EXAMPLE 27

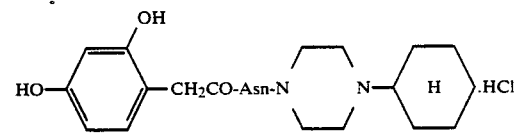

1-(2,4-Dihydroxyphenylacetyl-L-asparaginyl)-4-cyclohexylpiperazine.hydrochloride 1-(2,4-Dihydroxyphenylacetyl-L-asparaginyl)-4-phenylpiperazine (319 mg) obtained in Example 25 was subjected to catalytic reduction in the same manner as in Example 11 to obtain 1-(2,4-dihydroxyphenylacetyl-L-asparaginyl)-4-cyclohexylpiperazine.hydrochloride Mass spectrum (SIMS): m/z=445 ($M^+ + H^+$) ($C_{22}H_{32}N_4O_5$: M=444).

Elemental analysis for $C_{22}H_{32}N_4O_5 \cdot HCl$: Calcd. C: 56.34; H: 7.06; N: 11.95; Found C: 56.44; H: 6.88; N: 11.83.

EXAMPLE 28

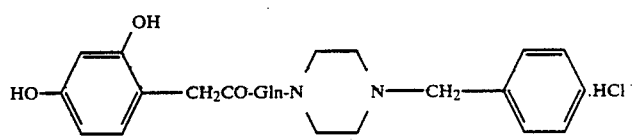

1-(2,4-Dihydroxyphenylacetyl-L-glutaminyl)-4-benzylpiperazine.hydrochloride (i) Condensation of 2,4-dibenzyloxyphenylacetic acid (718 mg) and 1-(N-tert-butoxycarbonyl-L-glutaminyl)-4-benzylpiperazine (1.0 g) was carried out in the same manner as in Example 12 (i) to obtain crystal (953 mg) of 1-(2,4-dibenzyloxyphenylacetyl-L-glutaminyl)-4-benzylpiperazine. Melting point: 120°–122° C.

Elemental analysis for $C_{38}H_{42}N_4O_5$: Calcd. C: 71.90; H: 6.67; N: 8.83; Found C: 71.73; H: 6.68; N: 8.80.

IR spectrum $\nu_{max}$ (KBr)cm$^{-1}$: 3450 (NH$_2$), 1680, 1660 (C=O), 1600 (Ph).

NMR spectrum $\delta_{ppm}$ (CDCl$_3$): 1.7–2.5 (8H, m), 3.3–3.7 (8H, m), 4.76 (1H, m), 5.00 (2H, s), 5.03 (2H, s), 6.5–7.4 (18H, m).

(ii) 1-(2,4-Dibenzyloxyphenylacetyl-L-glutaminyl)-4-benzylpiperazine (342 mg) obtained above was subjected to catalytic reduction in the same manner as in Example 15 to obtain colorless powder 1-(2,4-dihydroxyphenylacetyl-L-glutaminyl)-4-benzylpiperazine.hydrochloride (173 mg).

Mass spectrum (SIMS): m/z=455 (M$^+$+H$^+$) (C$_{24}$H$_{30}$N$_4$O$_5$: M=454).

Elemental analysis for C$_{24}$H$_{30}$N$_4$O$_5$.HCl: Calcd. C: 58.71; H: 6.36; N: 11.41; Found C: 58.89; H: 6.20; N: 11.72.

EXAMPLE 29

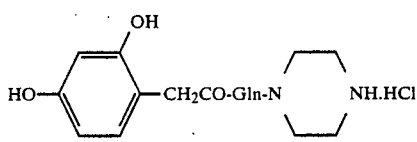

1-(2,4-Dihydroxyphenylacetyl-L-glutaminyl) piperazine.hydrochloride 1-(2,4-Dihydroxyphenylacetyl-L-glutaminyl)-4-benzylpiperazine.hydrochloride (104 mg) obtained in Example 28 was subjected to catalytic reduction in the same manner as in Example 9 to obtain colorless powder 1-(2,4-dihydroxyphenylacetyl-L-glutaminyl)piperazine. hydrochloride (74 mg).

Mass spectrum (SIMS): m/z=365 (M$^+$+H$^+$) (C$_{17}$H$_{24}$N$_4$O$_5$: M=364).

Elemental analysis for C$_{17}$H$_{24}$N$_4$O$_5$.HCl: Calcd. C: 50.93; H: 6.29; N: 13.98; Found C: 51.18; H: 6.28; N: 13.81.

EXAMPLE 30

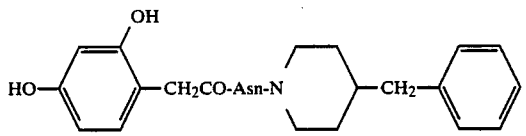

1-(2,4-Dihydroxyphenylacetyl-L-asparaginyl)-4-benzylpiperidine

In the same manner as in Example 1, 2,4-dibenzyloxyphenylacetyl-L-asparagine p-nitrophenyl ester (120 mg) obtained in Reference Example 1 and 4-benzylpiperidine (75 mg) were subjected to condensation and then catalytic reduction, resulting in elimination of protecting group to obtain crystalline powder of 1-(2,4-dihydroxyphenylacetyl-L-asparaginyl)-4-benzylpiperidine (71 mg).

Mass spectrum (SIMS): m/z=440 (M$^+$+H$^+$) (C$_{24}$H$_{29}$N$_3$O$_5$: M=439).

Elemental analysis for C$_{24}$H$_{29}$N$_3$O$_5$: Calcd. C: 65.58; H: 6.65; N: 9.56; Found C: 65.63; H: 6.60; N: 9.70.

EXAMPLE 31

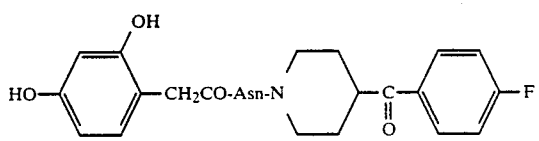

1-(2,4-Dihydroxyphenylacetyl-L-asparaginyl)-4-(4-fluorobenzoyl)piperidine

In the same manner as in Example 1, 2,4-dibenzyloxyphenylacetyl-L-asparagine p-nitrophenyl ester (100 mg) and 4-(4-fluoro)benzoylpiperidine (106 mg) were subjected to condensation and then catalytic reduction to eliminate protecting group to obtain powder of 1-(2,4-dihydroxyphenylacetyl-L-asparaginyl)-4-(4-fluoro)benzoylpiperidine (86 mg).

Mass spectrum(SIMS): m/z=472 (M$^+$+H$^+$) (C$_{24}$H$_{26}$N$_3$O$_6$: M=471).

Elemental analysis for C$_{24}$H$_{26}$N$_3$O$_6$: Calcd. C: 61.14; H: 5.56; N: 4.03; Found C: 61.17; H: 5.62; N: 3.82.

We claim:

1. A compound of the formula:

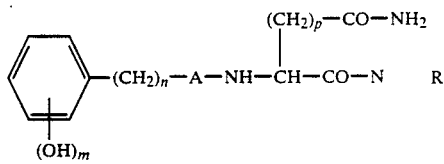

wherein

—N R represents a cyclic amino group of 6- to 24-membered ring having 2 to 6 nitrogen atoms in the ring, A represents a methylene group or a carbonyl group, m represents an integer of 1 to 3, n represents an integer of 0 to 4 and p represents an integer of 1 to 2, or a pharmaceutically acceptable salt thereof.

2. A salt according to claim 1 which is a hydrochloride.

3. A compound according to claim 1 namely, 1-(2,4-dihydroxyphenylacetyl-L-asparaginyl)piperazine.

4. A compound according to claim 1 namely, 1-(2,4-dihydroxyphenylacetyl-L-asparaginyl)-1,4,8,11-tetraazacyclotetradecane.

5. A compound according to claim 1 namely, 1-(2,4-dihydroxyphenylacetyl-L-asparaginyl)-1,4,7,10,13,16-hexaazacycloocatadecane.

6. A compound according to claim 1 namely 1-(2,4-dihydroxyphenylacetyl-L-asparaginyl)-1,4,7,10,13,16-hexaazacyclooctadecane.

7. A compound according to claim 1, namely 1-benzyl-4-(4-hydroxyphenylacetyl-L-asparaginyl)piperazine.

8. A compound according to claim 1, namely 1-benzyl-4-(L-asparaginyl)piperazine.

9. A compound according to claim 1, namely 1-(2,4-Dihydroxybenzoyl-L-asparaginyl)piperazine.

10. A compound according to claim 1, namely 1-(2,4-Dihydroxybenzoyl-L-glutaminyl)-4-phenylpiperazine.

11. A compound according to claim 1, namely 1-Benzoyl-4-(2,4-dihydroxybenzoyl-L-glutaminyl)piperazine.

12. A compound according to claim 1, namely 1-(2,4-Dihydroxybenzoyl-L-glutaminyl)piperazine.

13. A compound according to claim 1, namely 1-(2,4-Dihydroxybenzoyl-L-glutaminyl)-4-methylpiperazine.

14. A compound according to claim 1, namely 1-(2,4-Dihydroxybenzoyl-L-glutaminyl)-4-cyclohexylpiperazine.

15. A compound according to claim 1, namely 1-Benzyl-4-[3-(2,4-dihydroxyphenyl)propionyl-L-asparaginyl]piperazine.

16. A compound according to claim 1, namely 1-[3-(2,4-dihydroxyphenyl)propionyl-L-asparaginyl]piperazine.

17. A compound according to claim 1, namely 1-[3-(2,4-dihydroxyphenyl)propionyl-L-asparaginyl]-4-methylpiperazine.

18. A compound according to claim 1, namely 1-[3-(2,4-dihydroxyphenyl)propionyl-L-glutaminyl]-4-benzylpiperazine.

19. A compound according to claim 1, namely 1-[3-(2,4-dihydroxyphenyl)propionyl-L-glutaminyl]piperazine.

20. A compound according to claim 1, namely 1-[3-(2,4-dihydroxyphenyl)propionyl-L-glutaminyl]-4-methylpiperazine.

21. A compound according to claim 1, namely 1-[3-(2,4-dihydroxyphenyl)propionyl-L-asparaginyl]-4-phenylpiperazine.

22. A compound according to claim 1, namely 1-[3-(2,4-dihydroxyphenyl)propionyl-L-glutaminyl]-4-phenylpiperazine.

23. A compound according to claim 1, namely 1-[3-(2,4-dihydroxyphenyl)propionyl-L-asparaginyl]-4-cyclohexylpiperazine.

24. A compound according to claim 1, namely 1-[3-(2,4-dihydroxyphenyl)propionyl-L-glutaminyl]-4-cyclohexylpiperazine.

25. A compound according to claim 1, namely 1-(2,4-dihydroxyphenylacetyl-L-glutaminyl)-4-methylpiperazine.

26. A compound according to claim 1, namely 1-(2,4-dihydroxyphenylacetyl-L-asparaginyl)-4-methylpiperazine.

27. A compound according to claim 1, namely 1-(2,4-dihydroxyphenylacetyl-L-glutaminyl)-4-phenylpiperazine.

28. A compound according to claim 1, namely 1-(2,4-dihydroxyphenylacetyl-L-asparaginyl)-4-phenylpiperazine.

29. A compound according to claim 1, namely 1-(2,4-dihydroxyphenylacetyl-L-glutaminyl)-4-cyclohexylpiperazine.

30. A compound according to claim 1, namely 1-(2,4-dihydroxyphenylacetyl-L-asparaginyl)-4-cyclohexylpiperazine.

31. A compound according to claim 1, namely 1-(2,4-dihydroxyphenylacetyl-L-glutaminyl)-4-benzylpiperazine.

32. A compound according to claim 1, namely 1-(2,4-dihydroxyphenylacetyl-L-glutaminyl)piperazine.

* * * * *